US005889189A

United States Patent [19]
Rodriguez

[11] Patent Number: 5,889,189
[45] Date of Patent: Mar. 30, 1999

[54] PROCESS FOR PROTEIN PRODUCTION IN PLANTS

[75] Inventor: Raymond L. Rodriguez, Davis, Calif.

[73] Assignee: The Regents of the University of California, Oakland, Calif.

[21] Appl. No.: 458,422

[22] Filed: Jun. 2, 1995

Related U.S. Application Data

[63] Continuation-in-part of Ser. No. 153,563, which is a continuation of PCT/US94/13179 Nov. 15, 1994, Pat. No. 5,693,506.

[51] Int. Cl.$^6$ .......................... C12N 15/29; C12N 15/82; C12N 15/12; A01H 5/00
[52] U.S. Cl. .................. 800/205; 800/250; 800/DIG. 55; 800/DIG. 56; 800/DIG. 57; 800/DIG. 58; 435/69.1; 435/69.8; 435/172.3; 435/320.1; 536/23.6; 536/24.1; 536/23.5
[58] Field of Search ................................ 435/69.1, 320.1, 435/240.4, 172.3, 185, 69.7, 69.8, 419; 536/24.1, 23.6, 23.5, 23.4; 800/250, 205, DIG. 55, DIG. 56, DIG. 57, DIG. 58

[56] References Cited

U.S. PATENT DOCUMENTS

| 3,754,929 | 8/1973 | Palmer ........................................ 99/50 |
| 4,956,282 | 9/1990 | Goodman et al. ................... 435/69.51 |
| 5,202,422 | 4/1993 | Hiatt et al. ............................ 424/132.1 |
| 5,240,839 | 8/1993 | Serres et al. ......................... 435/172.3 |
| 5,460,952 | 10/1995 | Yu et al. ................................ 435/69.1 |

FOREIGN PATENT DOCUMENTS

| 0 290 395 | 11/1988 | European Pat. Off. . |
| 0 335 528 | 10/1989 | European Pat. Off. . |
| WO 90/01551 | 2/1990 | WIPO . |
| WO 91/02066 | 2/1991 | WIPO . |
| WO 91/13993 | 9/1991 | WIPO . |
| WO 92/13956 | 8/1992 | WIPO . |
| WO 94/11515 | 5/1994 | WIPO . |
| WO 95/06741 | 3/1995 | WIPO . |

OTHER PUBLICATIONS

Akazawa, T., and Hara–Nishimura, I., "Topographic Aspects of Biosynthesis, Extracellular Secretion, and Intracelular Storage of Proteins in Plant Cells," *Ann. Rev. Psychol.* 36:441–472 (1985).

An, G., et al., "Transformation of Tobacco, Tomato, Potato, and *Arabidopsis thaliana* Using a Binary Ti Vector System," 81:301–305 (1986).

Baulcombe, D.C., et al., "A novel wheat α–amylase gene (α–Amy3)," *Mol. Gen. Genet.* 209:33–40 (1987).

Belanger, F.C., et al., "Heat Shock Causes Destabilization of Specific mRNAs and Destruction of Endoplasmic Reticulum in Barley Aleurone Cells," *Proc. Natl. Acad. Sci. USA* 83:1354–1358 (1986).

Benfey, P.N., et al., "The CaMV 35S Enhancer Contains at Least Two Domains Which Can Confer Different Developmental and Tissue–Specific Expression Vectors," *EMBO J.* 8(8):2195–2202 (1989).

Benkel, B.F., and D.A. Hickey, "A Drosophila gene is subject to glucose repression," *Proc. Natl. Acad. Sci. USA* 84:1337–1339 (1987).

Bevan, M., "Binary Agrobacterium Vectors for Plant Transformation," *Nuc. Acids Res.* 12(22):8711 (1984).

Briggs, D.E., "Barley Germination: Biochemical Changes and Hormonal Control," in: *Barley: Genetics, Biochemistry, Molecular Biology and Biotechnology* (Shewry, P.R., Ed.) C.A.B. International, UK (1989).

Bytebier, B., et al., "T–DNA Organization in Tumor Cultures and Transgenic Plants of the Monocotyledon *Asparagus officinalis,*" *Proc. Natl. Acad. Sci. USA* 84:5345–5349 (1987).

Chan, M.–T., et al., "Transformation of Indica Rice (*Oryza sativa* L.) Mediated by *Agrobacterium tumefaciens,*" *Plant Cell Physiol.* 33(5):577–583 (1992).

Chandler, P.M., et al., "The effects of gibberellic acid and abscisic acid on α–amylase mRNA levels in barley aleurone layers studies using an α–amylase cDNA clone," *Plant Molecular Biology* 3:407–418 (1984).

Chang, H.–H., and Chan, M.–T., "*Agrobacterium tumefaciens*–Mediated Transformation of Soybean (*Glycine max* (L.) Merr.) is Promoted by the Inclusion of Potato Suspension Culture," *Bot. Bull. Academia Sinica* 32:171–178 (1991).

Christou, P., et al., "The Development of a Variety–Independent Gene–Transfer Method for Rice," *TIBTECH* 10:5 (1992).

Dale, P.J., et al., "Agroinfection of Wheat: Inoculation of In Vitro Grown Seedlings and Embryos," *Plant Science* 63:237–245 (1989).

Deikman, J., and Jones, R.L., "Control of α–Amylase mRNA Accumulation by Gibberellic Acid and Calcium in Barley Aleurone Layers," *Plant Physiol.* 78:192–198 (1985).

Depicker, A., et al., "Molecular Cloning of Overlapping Segments of the Nopaline Ti–Plasmid pTiC58 as a Means to Restriction Endonuclease," *Plasmid* 3:193–211 (1980).

Garfinkel, D.J., and Nester, E.W., "*Agrobacterium tumefaciens* Mutants Affected in Crown Gall Tumorigenesis and Octopine Catabolism," *J. Bacteriol.* 144(2):732–742 (1980).

Gillies, S.D., et al., "A Tissue–Specific Transcription Enhancer Element is Located in the Major Intron of a Rearranged Immunoglobulin Heavy Chain Gene," *Cell* 33:717–728 (1983).

(List continued on next page.)

*Primary Examiner*—Douglas W. Robinson
*Assistant Examiner*—Thomas Haas
*Attorney, Agent, or Firm*—Peter J. Dehlinger

[57] ABSTRACT

This invention provides for the secretion of heterologous protein in plant systems. In particular, this invention provides for the production of heterologous proteins by malting of monocot plant seeds. The heterologous genes are expressed during germination of the seeds and isolated from a malt. Also disclosed are chimeric genes, vectors and methods relating to the present invention. Protein production by cell culture techniques is also described.

12 Claims, 11 Drawing Sheets

OTHER PUBLICATIONS

Gould, J., et al., Transformation of *Zea mays* L. Using *Agrobacterium Tumefaciens* and the Shoot Apex, *Plant Physiol.* 95:426–434 (1991).

Graham, J., et al., "Use of the GUS Gene as a Selectable Marker for Agrobacterium–Mediated Transformation of Rubus," *Plant Cell, Tissue and Organ Culture* 20:35–39 (1990).

Hain, R., et al., "Uptake, Integration, Expression and Genetic Transmission of a Selectable Chimaeric Gene by Plant Protoplasts," *Mol. Gen. Genet.* 199:161–168 (1985).

Hernalsteens, J.P., et al., "An Agrogacterium–Transformed Cell Culture from the Monocot *Asparagus officinalis*," *EMBO J.* 3(13):3039–3041 (1984).

Hintz, W.E., and P.A. Lagosky, "A Glucose–Derepressed Promoter for Expression of Heterologous Products in the Filamentous Fungus *Aspergillus nidulans*," *Bio/Technology* 11:815–818 (1993).

Ho, T.–h., et al., "Regulation of Gene Expression in Barley Aleurone Layers," in *Molecular Biology of Plant Growth Control*, Alan R. Liss, Inc., pp. 35–39 (1987).

Holsters, M., et al., "Transfection and Transformation of *Agrobacterium tumefaciens*," *Mol. Gen. Genet.* 163:181–187 (1978).

Hooykaas, P.J.J., "Transformation of Plant Cells via Agrobacterium," *Plant Mol. Biol.* 13:327–336 (1989).

Huang, N., et al., "Structural organization and differential expression of rice α–amylase genes," *Nucleic Acids Research* 18(23):7007–7014 (1990).

Huang, N., et al., "Classification and evolution of α–amylase genes in plants," *Proc. Natl. Acad. Sci. USA* 89:7526–7530 (1992).

Huang, N., et al., "Classification and characterization of the rice α–amylase multigene family," *Plant Molecular Biology* 14:655–668 (1990).

Huang, N., et al., "RAmy2A; a novel α–amylase–encoding gene in rice," *Gene* 111:223–228 (1992).

Huang, N., et al., "Metabolic Regulation of α–Amylase Gene Expression in Transgenic Cell Cultures of Rice (*Oryza sativa* L.)," *Plant Mol. Biol.* 23:737–747 (1993).

Jacobsen, J.V., and Close, T.J., "Control of Transient Expression of Chimaeric Genes by Gibberellic Acid and Abscisic Acid in Protoplasts Prepared from Mature Barley Aleurone Layers," *Plant Mol. Biol.* 16:713–724 (1991).

Janssens, A., et al., "Plant Cells Induce Transcription of the *Agrobacterium tumefaciens* Nopaline pTiC58 Virulence Region," *Plant Sci.* 47:185–193 (1986).

Johnson, J.W., and Ascher, P., "Glycine Potentiates the NMDA Response in Cultured Mouse Brain Neurons," *Nature* 325:S29 (1987).

Jones, R.L., and J. MacMillan, "Gebberellins," in *Advanced Plant Physiology* (Wilkins, M.B., Ed.) Pitman Publishing Limited, London, pp. 21–52 (1984).

Karrer, E.E., et al., "Differential Expression of α–Amylase Genes in Germinating Rice and Barley Seeds," *Plant Mol. Biol.* 16:797–805 (1991).

Karrer, E.E., and Rodriguez, R.L., "Metabolic Regulation of Rice α–Amylase and Sucrose Synthase Genes in planta," *Plant J.* 2(4):517–523 (1992).

Karrer, E.E., et al., "Correlation Between α–Amylase Gene Expression and Seedling Vigor in Rice," *Euphytica* 66:163–169 (1993).

Khursheed, B., and Rogers, J.C., "Barley α–Amylase Genes: Quantitative Comparison of Steady–State mRNA Levels from Individual Members of the Two Different Families Expressed in Aleurone Cells," *J. Biol. Chem.* 263(35):18953 (1988).

Kim, J.–K., and Wu, R., "Nucleotide Sequence of a High–pI Rice (*Oryza sativa*)–Amylase Gene," *Plant Mol. Biol.* 18:399–402 (1992).

Knox, C.A.P., et al., "Structure and Organization of Two Divergent α–Amylase Genes from Barley," *Plant Mol. Biol.* 9:3–17 (1987).

Knudsen, S., and M. Müller, "Transformation of the developing barley endosperm by particle bombardment," *Planta* 185:330–336 (1991).

Koch, K.E., et al., "Sugar Levels Modulate Differential Expression of Maize Sucrose Synthase Genes," *Plant Cell* 4:59–69 (1992).

Kumagai, M.H., et al., "Expression and Secretion of Rice α–Amylase by *Saccharomyces cerevisiae*," *Gene* 94:209–216 (1990).

Lanahan, M.B., et al., "A Gibberellin Response Complex in Cerese α–Amylase Gene Promoters," *Plant Cell* 4:203–211 (1992).

Litts, J.C., et al., "The Isolation and Characterization of a Barley 1,3–1,4–β–Glucanase Gene," *Eur. J. Biochem.* 194:831–838 (1990).

Litts, J.C., et al., "Nucleotide Sequence of the Rice (*Oryza sativa*) Em Protein Gene (Emp1)," *Plant Mol. Biol.* 19:335–337 (1992).

Luo, Z.–x., and Wu, R., "A Simple Method for the Transformation of Rice Via the Pollen–Tube Pathway," *Plant Mol. Biol.* 6(3):165–174 (1988).

Maas, C., et al., "A Feedback Control Element Near the Transcription Start Site of the Maize Shrunken Gene Determines Promoter Activity," *EMBO J.* 9(11):3447–3452 (1990).

Maas, C., et al., "Applications of an optimized monocot expression vector in studying transient gene expression and stable transformation of barley," *Physiologia Plantarum* 85:367–373 (1992).

McElroy, D., et al., "Structural Characterization in a Rice Actin Gene," *Plant Mol. Biol.* 14:163–171 (1990).

O'Neill, S.D., et al., "The α–Amylase Genes in *Oryza sativa*: Characterization of cDNA Clones and mRNA Expression During Seed Germination," *Mol. Gen. Genet.* 2:235–244 (1990).

Pen, J., et al., "Phytase–containing Transgenic Seeds as a Novel Feed Additive for Improved Phosphorus Utilization," *Bio/Technology* 11:811–814 (1993).

Phillipson, B.A., "Expression of a Hybrid (1–3,1–4)–β–Glucanase in Barley Protoplasts," *Plant Sci.* 91:195–205 (1993).

Radke, S.E., et al., "Transformation of *Brassica napus* L. Using *Agrobacterium tumefaciens*: Developmentally Regulated Expression of a Reintroduced Napin Gene," *Theor. Appl. Genet.* 75:685–694 (1988).

Ranjhan, S., et al., "Chromosomal Localization and Genomic Organization of α–Amylase Genes in Rice (*Oryza sativa* L.)," *Theor. Appl. Genet.* 82:481–488 (1991).

Ritala, A., et al., "Stable Transformation of Barley Tissue Culture by Particle Bombardment," *Plant Cell Reports* 12:435–440 (1993).

Rodriguez, R.L., et al., "Organization, structure, and expression of the rice α–amylase multigene family," *Rice Genetics* 11:417–429 (1990).

Rogers, J.C., "Two Barley α–Amylase Gene Families Are Regulated Differently in Aleurone Cells," *The Journal of Biological Chemistry* 260(6):3731–3738 (1985).

Rogers, J.C., and Milliman, C., "Coordinate Increase in Major Transcripts from the High pI α–Amylase Multigene Family in Barley Aleurone Cells Stimulated with Gibberellic Acid," *J. Biol. Chem.* 259(19):12234 (1984).

Rothstein, S.J., et al., "Synthesis and secretion of wheat α–amylase in *Saccharomyces cerevisiae*," *Gene* 55:353–356 (1987).

Shah, S.V., et al., "Corn Metabolites Affect Growth and Virulence of *Agrobacterium tumefaciens*," *Proc. Natl. Acad. Sci. USA* 87:3879 (1990).

Schäfer, W., et al., "T–DNA Integration and Expression in a Monocot Crop Plant After Induction of Agrobacterium," *Nature* 327:529 (1987).

Schläppi, M., and Hohn, B., "Competence of Immature Maize Embryos for Agrobacterium–Mediated Gene Transfer," *Plant Cell* 4:7–16 (1992).

Sfat, M.R., et al., "Malts and Malting," *K. Othmer. Ency. Chem.* 14:810 (1981).

Sheen, J., "Metabolic Repression of Transcription in Higher Plants," *The Plant Cell* 2:1027–1038 (1990).

Simmons, C.R., et al., "Strucure of a Rice β–Glucanase Gene Regulated by Ehtylene, cytokinin, Wounding, Salicylic Acid and Fungal Elicitors," *Plant Mol. Biol.* 18:33 (1992).

Simmons, C.R., and R.L. Rodriguez, "High–Level Synthesis and Secretion of α–Amylase from Rice Callus," in *Biocatalysis in Agricultural Biotechnology* (Whitaker and Sonnet, Eds.) American Chemical Society, Washington, D.C., pp. 202–214 (1989).

Stachel, S.E., et al., "Identification of the Signal Molecules Produced by Wounded Plant Cells that Activate T–DNA Transfer in *Agrobacterium tumefaciens*," *Nature* 318:624 (1985).

Sutliff, T.D., et al., "Characterization of an α–amylase multigene cluster in rice," *Plant Molecular Biology* 16:579–591 (1991).

Usami, S., et al., "Factor Inducing *Agrobacterium tumefaciens* vir Gene Expression is Present in Monocotyledonous Plants," *Proc. Natl. Acad. Sci. USA* 85:3748 (1988).

Weiher, H., et al., "Multiple Point Mutations Affecting the Simian Virus 40 Enhancer," *Science* 219.

Whittier, R.F., et al., "Nucleotide sequence analysis of alpha–amylase and thiol protease genes that are hormonally regulated in barley aleurone cells," *Nucleic Acids Research* 15(6):2515–2535 (1987).

Wilmink, A., and J.J.M. Dons, "Selective Agents and Marker Genes for Use in Transformation of Monocotyledonous Plants," *Plant Molecular Biology Reporter* 11(2):165–185 (1993).

Wirsel, S., et al., "Three α–amylase genes of *Aspergillus oryzae* exhibit identical intron–exon organization," *Molecular Microbiology* 3(1):3–14 (1989).

Xiaolan, D., and Shanbao, C., "Variation of the Characterizations in Rice (*Oryza sativa*) Induced by Foreign DNA Uptake," (Abstract).

Xiaolan, D., and Shanbao, C., "Expression of Exogenous DNA Introduced Directly into Rice (*Oryza sativa*)," *Gen. Manip. of Crops* 4:22 (1988).

Yang, N.–S., and Russell, D., "Maize Sucrose Synthenase–1 Promoter Directs Phloem Cell–Specific Expression of Gus Gene in Transgenic Tobacco Plants," *Proc. Natl. Acad. Sci. USA* 87:4144 (1990).

Yu, S.–M., et al., "Metabolic Derepression of α–Amylase Gene Expression in Suspension–Cultured Cells of Rice," *J. Biol. Chem.* 296(31):21131 (1991).

Yu, S.–M., et al., "Regulation of α–amylase–encoding gene expression in germinating seeds and cultured cells of rice," *Gene* 122:247–253 (1992).

Zaenen, I., et al., "Supercoiled Circular DNA in Crown–Gall Inducing Agrobacterium Strains," *J. Mol. Biol.* 86:109–127 (1974).

Zenk, M.H., "T. Chasing the enzymes of secondary metabolism: Plant cell cultures as a pot of gold," *Phytochemistry* 30(12):3861–3863 (1991).

RAmy3D PROMOTER/GUS FUSION

RAmy1A PROMOTER/GUS FUSION

AVERAGE GUS ACTIVITY (nM/min/mg)

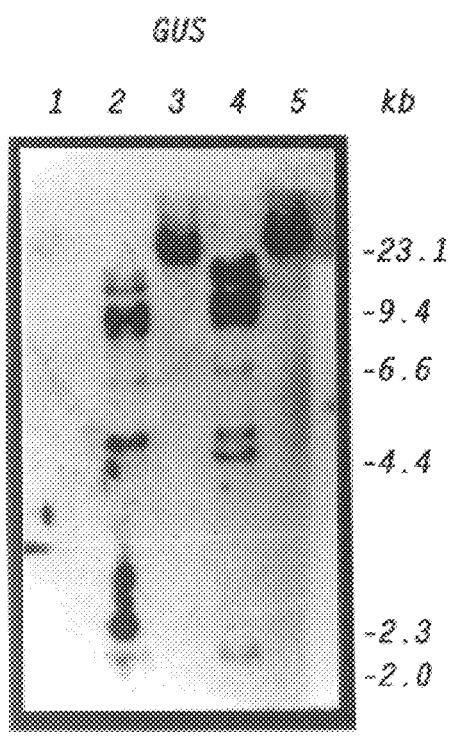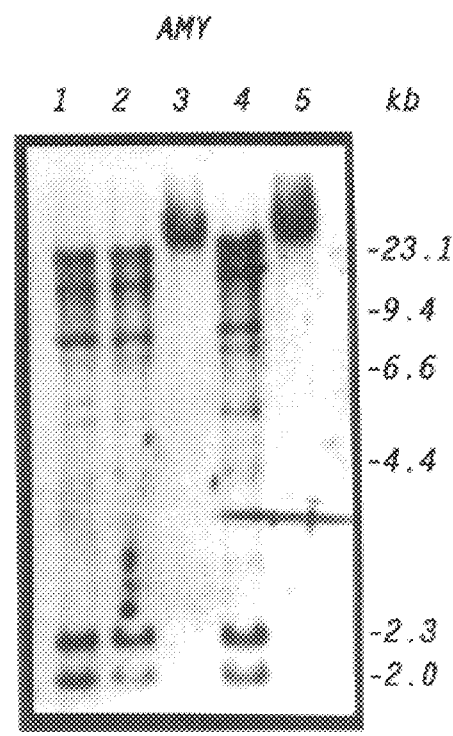

TIME AFTER SUBCULTURE INTO
SUCROSE-FREE MEDIUM (HRS)

| RAmy 3D | -264 | GAGACCGGGCCCCGACGCGGCCGACGCGGCG | (SEQ ID NO: 3) |
| RAmy 3E | -392 | GAGAGCTCGCGCCGCCTCGATCGGCGCGGCG | (SEQ ID NO: 4) |

| RAmy 3D | -648 | TTCCGGCTGC | (SEQ ID NO: 5) |
| RAmy 3E | -479 | TTGCGGCTTGC | (SEQ ID NO: 6) |

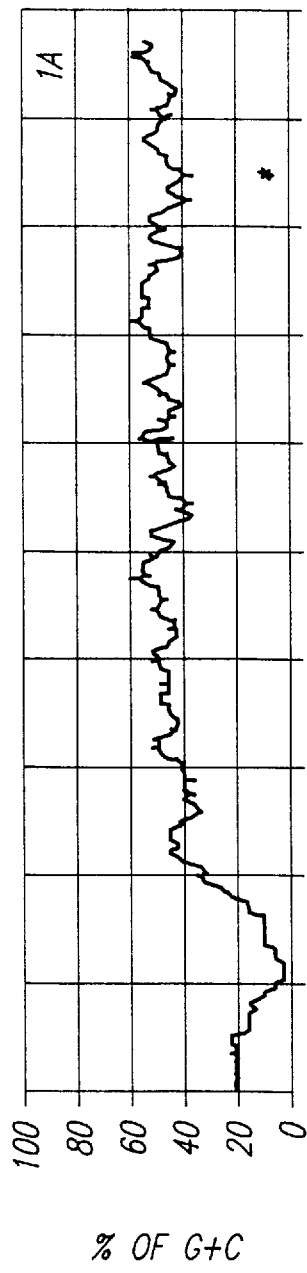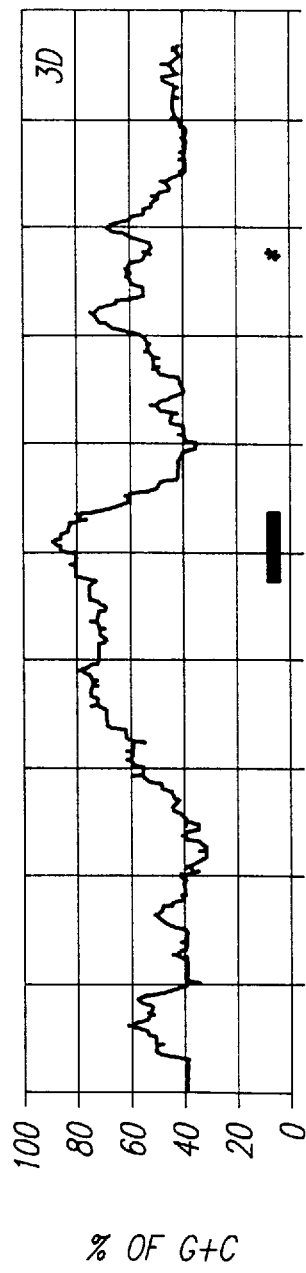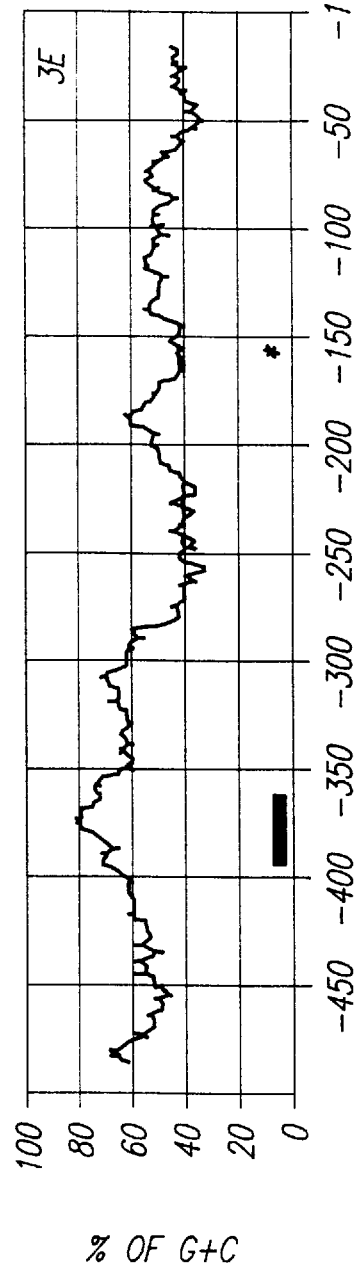
FIG. 6A
FIG. 6B
FIG. 6C

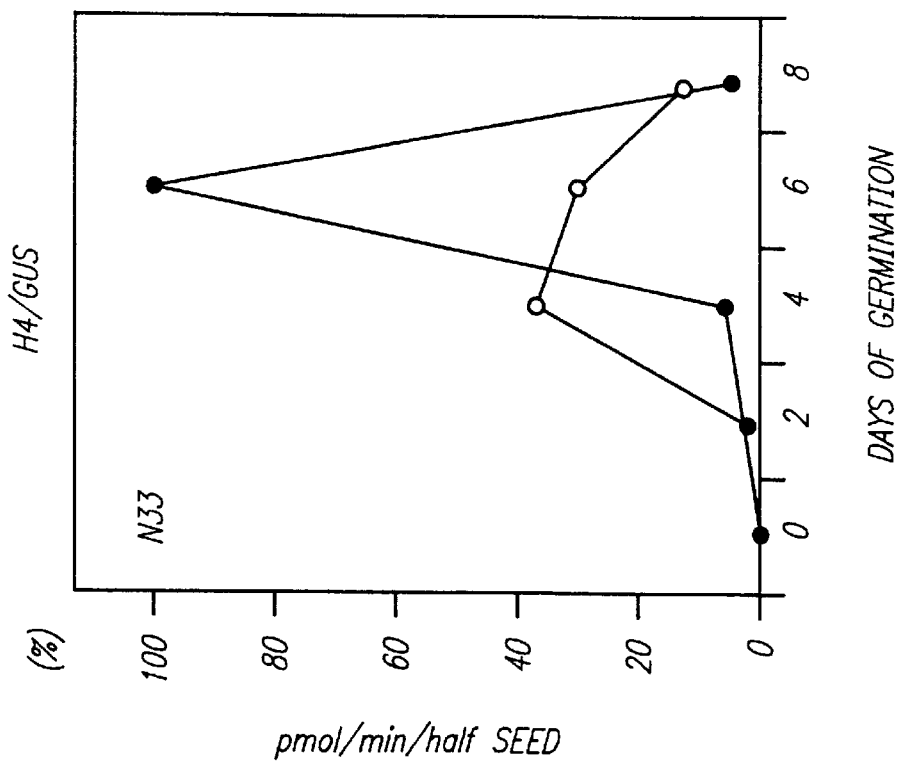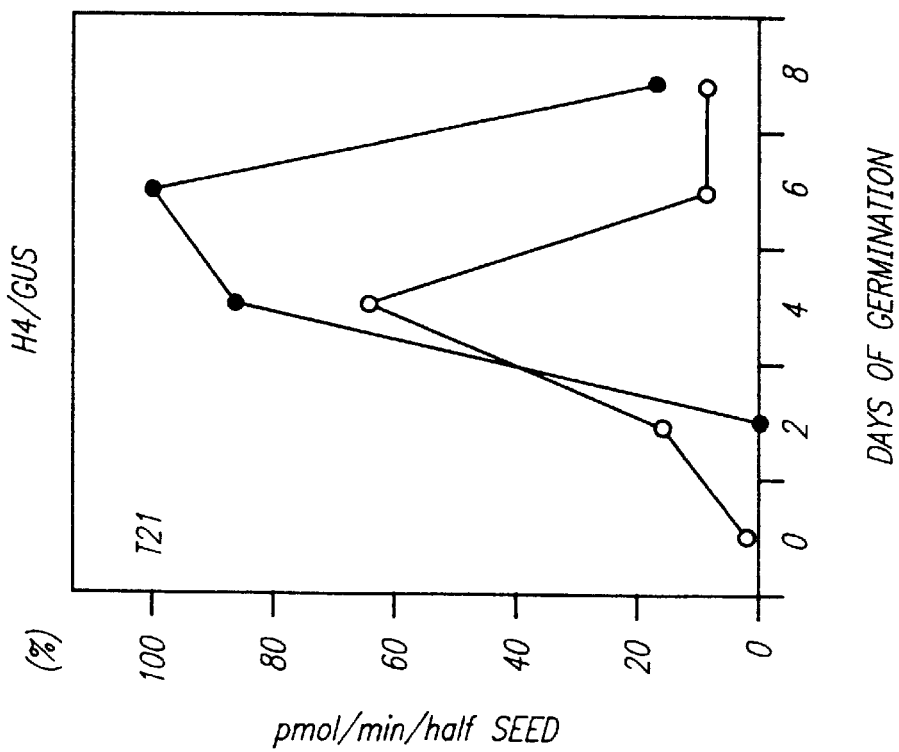

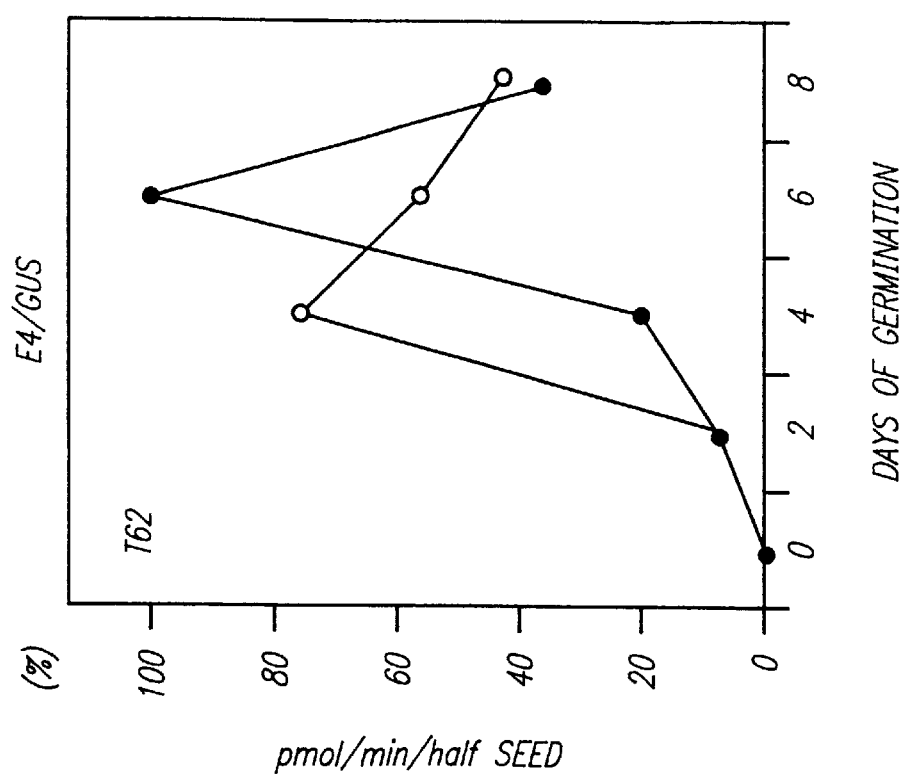
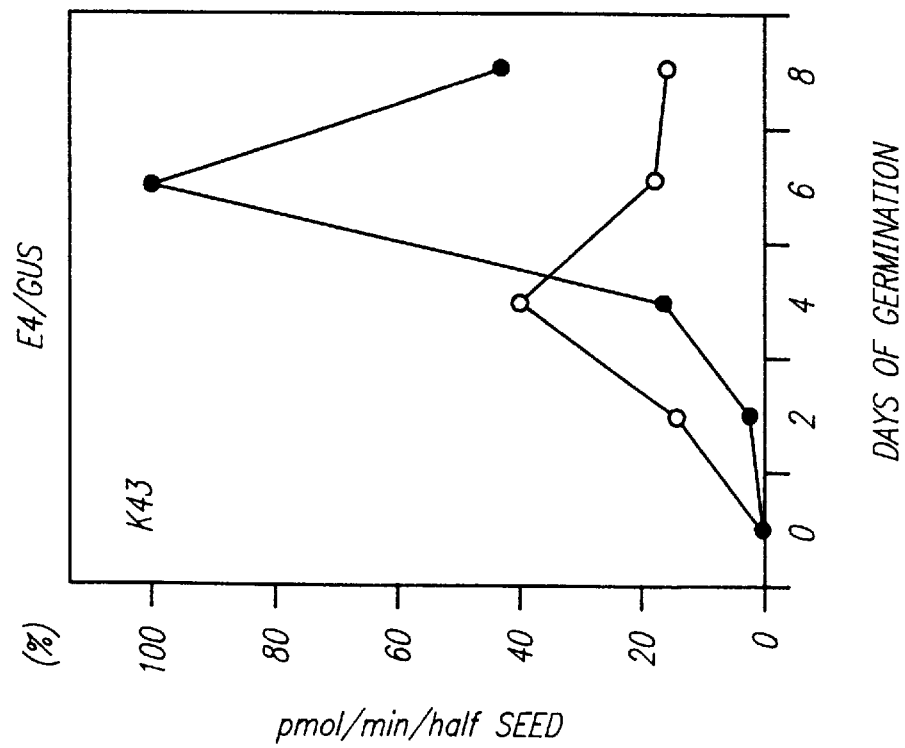

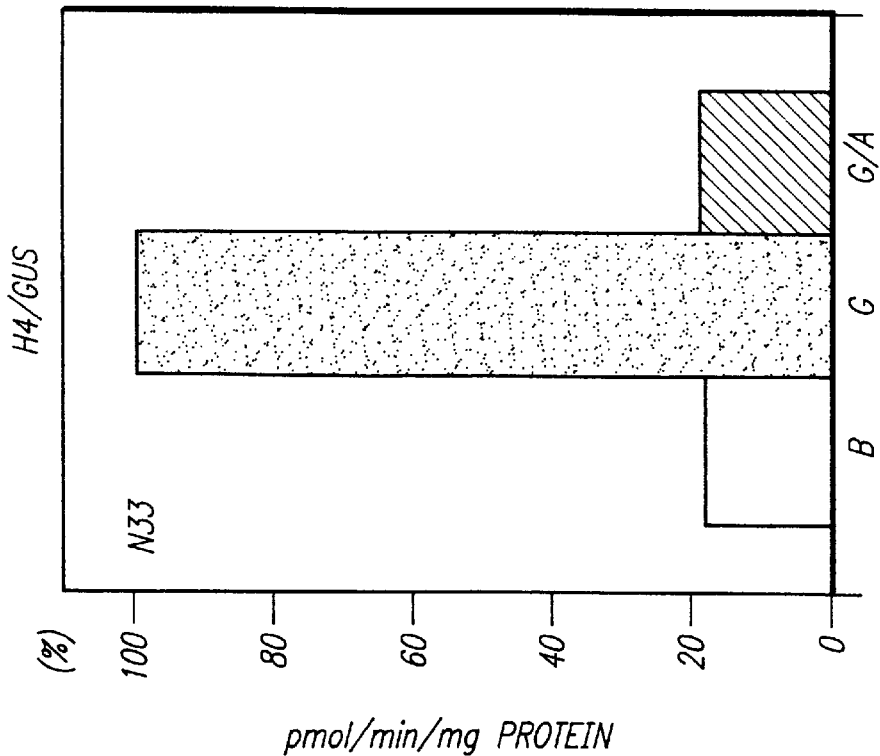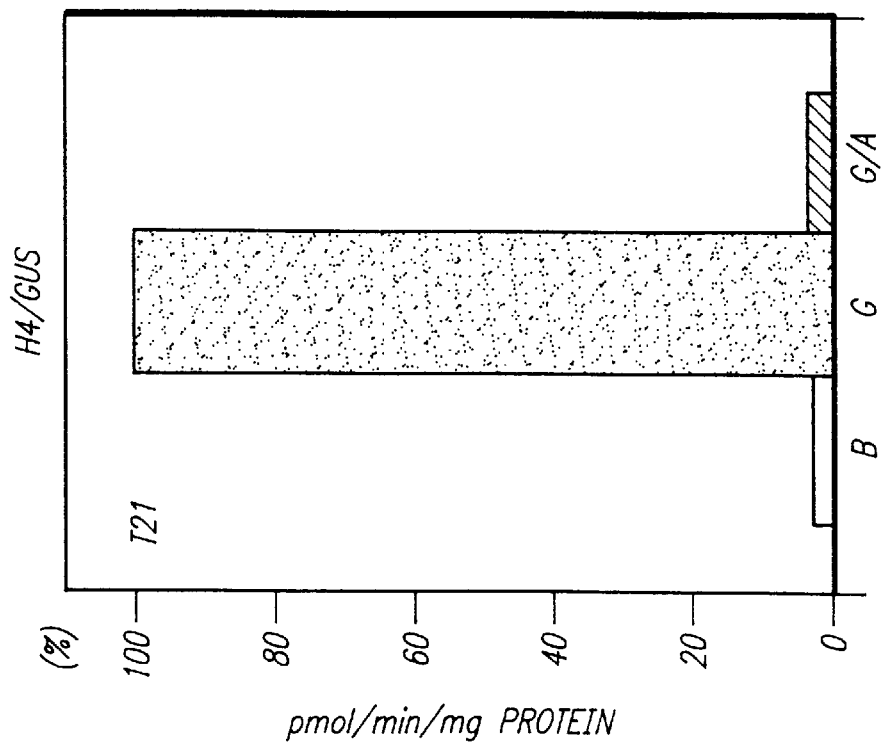

ptPROCESS FOR PROTEIN PRODUCTION IN PLANTS

This application is a continuation of PCT/US94/13179 filed 15 Nov. 1994, herein incorporated by reference, and a continuation-in-part of U.S. Ser. No. 08/153,563, filed 16 Nov. 1993, now U.S. Pat. No. 5,693,506 herein incorporated by reference.

FIELD OF THE INVENTION

The field of this invention is production of polypeptides in germinating plant seeds employing the malting process. The invention also relates to plant expression vectors, chimeric genes and plant cell culture methods.

BACKGROUND OF THE INVENTION

The ability to clone and produce a wide range of proteins from diverse sources became feasible with the advent of recombinant technology. The selection of expression hosts for commercial biotechnology proteins is based on the economics of fermentation and purification as well as the ability of the host to accomplish the post-translational modifications needed for full biological activity of the recombinant protein. Some of these post-translational modifications include: signal peptide processing, pro-peptide processing, protein folding, disulfide bond formation, glycosylation, gamma carboxylation and beta-hydroxylation. Some of the economic factors influencing the choice of an expression host include: rates of biomass production, equipment costs, medium composition and expense, processes for protein recovery and purification, product yields, and the potential for contamination.

Much of the early work in biotechnology was directed toward the expression of recombinant or "heterologous" proteins in prokaryotes, like *Escherichia coli* and *Bacillus subtilis*. Such work in procaryotes provided ease of genetic manipulation, growth of the organisms in batch culture and the possibility of large-scale fermentation.

*E. coli* can perform signal peptide processing, protein folding, and disulfide bond formation. However, it cannot secrete proteins extracellularly glycosylate, gamma carboxylate, beta hydroxylate or process propeptides. *B. subtilis* suffers from the same limitations *E. coli* except that it is capable of extracellular secretion.

Total production costs from bacteria are also high because of problems with product recovery, purification, and the inability of bacteria to perform many of the post-translational modifications mentioned above. Furthermore, *E. coli* and other bacteria are pathogens and contaminants, such as, pyrogens and endotoxins, must be removed from the recombinantly produced protein. In addition, extensive post-purification chemical and enzymatic treatments (e.g., to refold the protein into an active form) can be required to obtain biologically active protein.

Because proteins are not secreted from prokaryotes, like *E. coli*, such cells must be disrupted for product recovery. The subsequent release of bacterial contaminants and other proteins make product purification more difficult and expensive. Because purification accounts for up to 90% of the total cost of producing recombinant proteins in bacteria, proteins, like tissue Plasminogen Activator (tPA), can cost several thousand dollars per gram to produce from *E. coli*.

Because of the many inadequacies associated with prokaryotic hosts, the biotechnology industry has looked to eukaryotic hosts like mammalian cell tissue culture, yeast, fungi, insect cells, and transgenic animals, to properly and efficiently express recombinant proteins. However, these hosts can suffer from any or all of the following disadvantages: expensive fermentation, low yields, secretion problems, inappropriate modifications in protein processing, high operating costs, difficulties in scaling up to large volumes, and/or contamination that either kills the host culture or makes product purification more expensive. For these reasons, existing eukaryotic hosts are unable to provide high-volume, low-cost protein production of recombinant proteins.

For most of those proteins requiring extensive post-translational modifications for therapeutic and/or functional activity, mammalian cell culture is the most common alternative to *E. coli*. Although mammalian cells are capable of correctly folding and glycosylating bioactive proteins, the quality and extent of glycosylation can vary with different culture conditions among the same host cells. Furthermore, mammalian culture has extremely high fermentation costs (60–80% of total production expense), requires expensive media, and poses safety concerns from potential contamination by viruses and other pathogens. Yields are generally low, for example, in the range of 0.5–1.5% of cellular protein, or up to about 300–400 milligrams per liter.

Yeast, fungi, insect cells and transgenic animals are currently being used as alternatives to mammalian cell culture. Yeast, however, produces incorrectly glycosylated proteins that have excessive mannose residues and generally limited eukaryotic processing. Further, although the baculovirus insect cell system can produce high levels of glycosylated proteins, these are not secreted—making purification complex and expensive. Fungi represent the best current system for high-volume, low-cost production, but they are not capable of expressing many target proteins. Transgenic animals are subject to lengthy lead times to develop herds with stable genetics, high operating costs, and contamination by animal viruses.

The biochemical, technical and economic limitations on existing prokaryotic and eukaryotic expression systems has created substantial interest in developing new expression systems for recombinant proteins. Plants represent the most likely alternative to existing systems because of the advantageous economics of field-grown crops, the ability to synthesize proteins in storage organs like tubers, seeds, fruits and leaves and the ability of plants to perform many of the post-translational modifications previously described. However, existing plant expression systems suffer from low yield (<1.5% of total cellular protein).

Furthermore, expression of the target protein occurs in the open field (in roots, stems, leaves, fruits and seeds), thus making it difficult to prevent the recombinant protein from entering the food and feed chain. This is an issue of much concern to government regulatory agencies.

Although the use of plant cell culture to express proteins has been discussed, the lack of knowledge about the genetics and biochemistry of plant gene expression and secretion has precluded this system from being developed into a commercially feasible one.

RELEVANT LITERATURE

The potential for the use of plant cell cultures to product proteins has been described by Zenk, *Phytochemistry* 30:3861–3863 (1991). Descriptions of the rice amylase genes may be found in Huang, et al., *Proc. Natl. Sci. U.S.A.* 89:7526–7530 (1992); Huang, et al., *Plant, Molecular Biology* 14:655–668 (1990); Huang, et al., *Nucleic Acids*

Research 18:7007–7014 (1990); Huang, et al., *Gene* 11 1:223–228 (1992); Rodriguez, et al.: Organization Structure and Expression of the Rice α-Amylase Multigene Family. *Second International Rice Genetics Symposium. Rice Genetics* 11:417–429 (1990); Sutliff, et al., *Plant Molecular Biology* 16:579–591 (1991). The promoter sequences for the rice amylase genes are described in Huang, et al., *Nucleic Acids Research* 18:7007–7014 (1990). Descriptions of plant protein signal peptides may be found in addition to the references described above in Vaulcombe, et al., *Mol. Gen. Genet.* 209:33–40 (1987); Chandler, et al., *Plant Molecular Biology* 3:407–418 (1984); Rogers, *J. Biol. Chem.* 260:3731–3738 (1985); Rothstein, et al., *Gene* 55:353–356 (1987); Whittier, et al., *Nucleic Acids Research* 1 5:251 5–2535 (1987); Wirsel, et al., *Molecular Microbiology* 3:3–14 (1989); Yu, et al., *Gene* 122:247–253 (1992).

A description of the regulation of plant gene expression by the phytohormone, gibberellic acid and secreted enzymes induced by gibberellic acid can be found in R. L. Jones and J. MacMillin, Gibberellins: in: *Advanced Plant Physiology*,. Malcolm B. Wilkins, ed., 1984 Pitman Publishing Limited, London, pp. 21–52. References that describe other metabolically-regulated genes: Sheen, *Plant Cell*, 2:1027–1038(1990); Maas, et al., *EMBO J.* 9:3447–3452 (1990); Benkel and Hickey, *Proc. Natl. Acad. Sci.* 84:1337–1339 (1987).

SUMMARY OF THE INVENTION

The present invention has two aspects. In the first aspect, the invention describes the production of high levels of recombinant proteins by seeds during the malting process. The invention includes a method of producing a protein or polypeptide in a monocot plant seed. Monocot plant seeds typically contain an endosperm surrounded by an aleurone or scutellar epithelium layer. Embryo development takes place within the endosperm. In the method, seeds are provided that contain a chimeric gene having at least the following components: (i) a transcriptional regulatory region inducible during seed germination, (ii) a heterologous first DNA sequence encoding the protein, and (iii) a second DNA sequence encoding signal polypeptide. The second DNA sequence is operably linked to the transcriptional regulatory region and the first DNA sequence. The signal polypeptide encoded by the second DNA sequence is in translation-frame with the protein and is effective to facilitate secretion of the protein across the aleurone or scutellar epithelium layer into the endosperm. The seeds are malted under conditions to induce expression of the transcriptional regulatory region and production of the protein or polypeptide of interest.

In this method, the leader sequence may be omitted from the chimeric gene construct if secretion of the protein of interest is not required, for example, for production of a mash or malted seed product intended for veterinary use.

In the above method, the seed may be obtained from a cereal plant, including, but not limited to wheat, rice, oats, rye, corn, sorghum, millet or barley. Barley and rice seeds are preferred embodiments.

The transcriptional regulatory region of the chimeric gene used in the practice of the present invention can be obtained, for example, from one of the following groups: α-amylase genes, sucrose synthase genes and sucrose-6-phosphate synthetase genes. Examples of α-amylase genes include the following genes obtained from rice and their homologs in other monocots: RAmy1A (SEQ ID NO:2), RAmy3B, RAmy3C, RAmy3D, HV18 (SEQ ID NO:1) and RAmy3E.

In one embodiment of the invention the RAmy3D gene or homologs thereof is used.

Expression of the transcription regulatory region of the chimeric gene can be specifically regulatable by a small molecule. Examples of such small molecules include plant hormones, cytokines and metabolites. Exemplary small molecules include, but are not limited to, absisic acid, gibberellic acids, indoleacetic acids, kinetins, butyric acid, oxalic acid, acetic acid, okadakic acid or arachidonic acid. In one embodiment, the transcription regulatory region is from the RAMY3D gene, or a homolog thereof, and the small molecule is absisic acid.

The malting step of the present method can also include the addition or removal of a small molecule in an amount effective to stimulate production of the protein.

Other embodiments of the transcriptional regulatory region of the chimeric gene includes regulatory regions sucrose synthase genes or sucrose-6-phosphate synthetase genes. With these promoters useful regulatory small molecules include sugar (e.g., glucose or sucrose), sugar-phosphates, or other sugar-derivative molecules.

The protein produced by the method of the present invention can be selected from any number of sources. Exemplary classes of proteins or polypeptides include, but are not limited to, the following: enzymes, antibodies, growth factors, cytokines, hormones, or antigens (e.g., vaccines). Specific proteins or polypeptides include, but are not limited to, the following: α-antitrypsin, antithrombin 3, fibrinogen, human serum albumin, factor VIII, granulocyte colony-stimulating factor and granulocyte macrophage colony-stimulating factor. The protein may also be an industrial protein (e.g., xylanase, oxidoreductase, peroxidase, glucanase, α-amylase, phytase or glucose oxidase).

The signal polypeptide (or signal sequence) can be obtained from a number of sources. Exemplary gene-sources for the signal sequence are α-amylase genes, sucrose synthase genes and sucrose-6-phosphate synthetase genes. Examples of α-amylase genes include the following genes obtained from rice and their homologs in other monocots: RAmy1A (SEQ ID NO:2), RAmy3B, RAmy3C, RAmy3D, HV18 (SEQ ID NO:1) and RAmy3E.

The method of the present invention can also include isolation or partial purification of the protein or polypeptide of interest.

In another embodiment, the method of the invention includes separation of the embryo from the endosperm of the seed. In this embodiment, the embryo is (i) separated from the other seed parts, and (ii) germinated under conditions that induce expression of the transcriptional regulatory region and production of the protein. The seeds used in the malting process may have one or more chimeric genes, where the genes have the same or different transcription regulatory regions. The method may include separating the embryos and germinating them under conditions that (i) induce expression of the transcriptional regulatory region of the second chimeric gene, and (ii) production of the polypeptide of the second chimeric gene. The transcriptional regulatory region can, for example, be selected from those described above. The method may also include separating embryos of the seed from the endosperm, contacting the endosperm with the plant hormone which induces expression of the expression cassette, and isolating the heterologous protein from the endosperm.

Also included in the present invention are the germinated seed, malted seed and mash products by the above-described method. These products may be directly used in veterinary applications where purification of the expressed protein or polypeptide is not required (e.g., growth hormone or vaccines).

In another aspect the invention includes the above-described chimeric gene constructs. Further, the invention includes plant expression vectors carrying the chimeric genes, plant cells bearing the chimeric gene or transformed by such vectors, and transgenic plants bearing the chimeric gene. The transgenic plants and plant cells can, for example, be selected from the following group: rice, wheat, oats, rye, corn, sorghum, millet, and barley.

The present invention also includes transgenic seeds produced by the transgenic plants of the present invention. Such transgenic seeds carry the chimeric gene of the present invention.

In the second aspect of the present invention, a plant cell culture system is described for the production of recombinant proteins. The cells for the culture system are preferably derived from scutellar tissue. The cells used in this aspect of the present invention are transgenic and contain a chimeric gene. The chimeric gene contains at least the following elements: (i) a transcription regulatory region inducible during seed germination, where expression mediated by the region is specifically regulatable by a small molecule, and (ii) a heterologous DNA sequence that encodes the polypeptide, where the DNA sequence is operably linked to transcription regulatory region or promoter.

The chimeric genes can be constructed using the components described above, including the transcription regulatory region, proteins or polypeptides for expression, and regulatory small molecules.

The invention includes plant expression vectors carrying the chimeric genes, plant cells bearing the chimeric gene or transformed by such vectors, and transgenic plants bearing the chimeric gene. The transgenic plants and plant cells can, for example, be selected from the following group: rice, wheat, oats, rye, corn, sorghum, millet, and barley.

In one embodiment, the second aspect of the invention includes a method for modulating expression of a polypeptide in plant tissue cell culture. In this method the cells are the transgenic cells just described, typically from scutellar epithelium. These cells, carrying the chimeric gene, are cultured under conditions that facilitate plant cell growth. Expression of the transcription regulatory region is modulated by addition or removal of the regulatory small molecule to the plant cell culture.

Cells used in this aspect of the invention are monocot cells from, for example, wheat, rice, oats, rye, corn, sorghum, millet or barley.

Modulation of expression can be accomplished by inhibition or induction. In one embodiment, the modulation is an inhibition of expression and the small molecule is a sugar or sugar-phosphate derivative. In another aspect, the modulation is an induction of expression and the small molecule is a plant hormone. Selected plant hormones can also be used to inhibit expression.

In the method, the culturing step can further include the addition or removal of sugar or sugar-derivatives in an amount effective to stimulate production of the heterologous protein. In another embodiment, modulation is the enhancement of expression of the polypeptide in plant tissue cell culture and the enhancement is accomplished by addition of a small molecule to the plant cell culture, where the small molecule specifically induces expression from the transcription regulatory region. An exemplary embodiment of this type of modulation is the use of the transcription regulatory region from the RAMY3D gene, or a homolog thereof, and where the small molecule is abscisic acid.

This aspect of the invention includes production and isolation or partial purification of the protein or polypeptide of interest.

The invention also includes the following method of producing a polypeptide in plant cells. The transgenic plant cells described above are cultured in vitro (i) under conditions that facilitate plant cell growth, and (ii) in the presence of a small molecule that inhibits expression from the transcription regulatory region. The small molecule is present at a concentration effective to repress expression from the transcription regulatory region. The concentration of this small molecule is then reduced in the culture to a level that permits expression from the transcription regulatory region and allows production of the polypeptide. Exemplary small molecules for the practice of this embodiment of the invention include sugars or sugar-phosphate derivatives. After removal of the inhibitory small molecule, a second small molecule can be added to induce expression from the promoter present in the chimeric gene.

The invention also includes (i) an isolated DNA sequence essentially consisting of the nucleic acid sequence of SEQ ID NO:1 or SEQ ID NO:2; an isolated DNA sequence essentially consisting of a transcriptional regulatory region obtained from SEQ ID NO:1 or SEQ ID NO:2; and (iii) one of these isolated DNA sequences operably linked to a heterologous DNA sequence encoding a protein. Such isolated DNA sequences may also include a second DNA sequence encoding signal polypeptide. The second DNA sequence is operably linked to the transcriptional regulatory region and the heterologous DNA sequence. Further, the encoded signal polypeptide is in translation-frame with the protein encoded by the heterologous DNA sequence.

These and other objects and features of the invention will be more fully appreciated when the following detailed description of the invention is read in conjunction with the accompanying drawings.

BRIEF DESCRIPTION OF THE FIGURES

FIGS. 3A and 3B show two Southern blot hybridizations, where FIG. 3A depicts DNA isolated from control (lane 1) and 3DG cells (lanes 2–5) and probed with a GUS gene (GUS) probe, and FIG. 3B represents the same DNA fractions probed with a rice α-amylase gene (AMY) probe.

FIGS. 6A to 6C provide a comparison of G+C content for three different α-amylase promoters.

FIGS. 9A to 9D are depictions of fluorometric measures of the expression of GUS in two H4/GUS transgenic lines (T21 and N33) (FIGS. 9A and 9B), and two E4/GUS transgenic lines (K43 and T62) (FIGS. 9C and 9D).

FIGS. 10A–10D provide graphic depictions of four fluorometric measures of the expression of GUS in two H4/GUS transgenic lines (T21 and N33) (FIGS. 10A and 10B), and two E4/GUS transgenic lines (K43 and T62) (FIGS. 10C and 10D), quantifying the induction of GUS by addition of gibberellic acid.

DETAILED DESCRIPTION OF THE INVENTION

I. Definitions

Figure 1A:
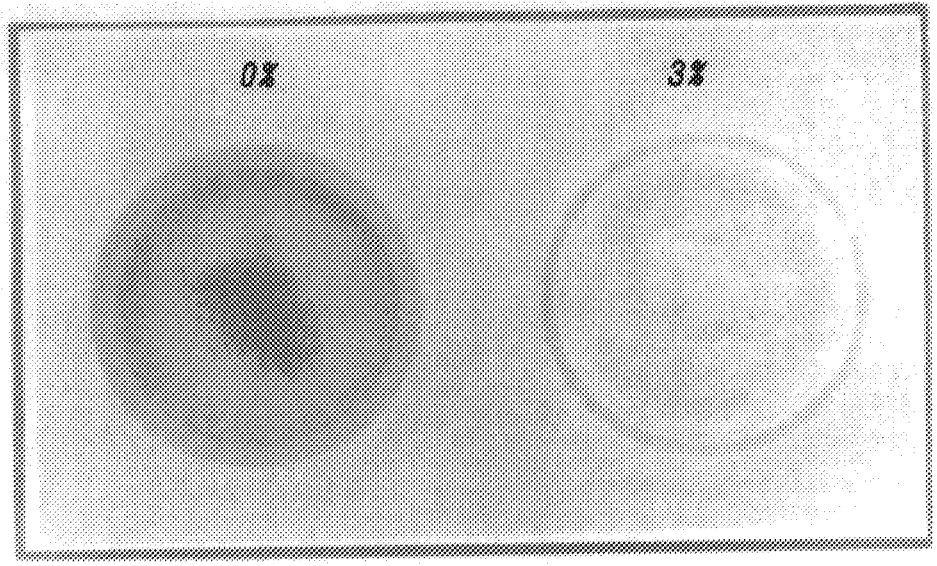
FIG. 1A is a full color photograph of the expression of the GUS gene in cell culture.

"Cell culture" refers to cells and cell clusters both protoplast and callus tissue that are without differentiated cells or organs and are growing on a growth media.

"In an amount effective" refers to an amount that is suitable to produce the desired effect in a measurable and reproducible amount.

"Inducible" means a promoter that is turned on by the presence or absence of a cell hormone or metabolite. It includes both indirect and direct inducement.

"Inducible during germination" refers to promoters which are substantially silent but not totally silent prior to germination but are turned on substantially (greater than 25%) during germination and development in the seed. Examples of promoters that are inducible during germination are presented below.

"Homologous DNA" refers to DNA not introduced into the plant or plant host by recombinant means.

"Heterologous DNA" refers to DNA which has been transfected into plant cells. Typically, heterologous DNA refers to DNA that is not originally derived from the transfected or transformed cells' genomic DNA (e.g., GUS gene sequences). A DNA sequence may also be heterologous to an adjacent DNA sequence, for example, a DNA sequence is heterologous to a promoter or transcription regulatory region, when the promoter or transcription regulatory region is not native, that is, not naturally occurring adjacent the DNA sequence of interest.

A "transcription regulatory region" typically refers to nucleic acid sequences that influence and/or promote initiation of transcription, such as promoters. Promoters are typically considered to include regulatory regions, such as enhancer or inducer elements.

A "chimeric gene," in the context of the present invention, typically comprises a promoter sequence operably linked to non-homologous DNA sequences that encode a gene product (e.g., a RAmy3D promoter adjacent DNA sequences encoding human serum albumin). A chimeric gene may also contain further transcription regulatory elements, such as transcription termination signals, as well as translation regulatory signals, such as, termination codons.

"Operably linked" refers to components of a chimeric gene or an expression cassette that function as a unit to express a heterologous protein. For example, a promoter operably linked to a heterologous DNA, which encodes a protein, promotes the production of functional mRNA corresponding to the heterologous DNA.

A "product" encoded by a DNA molecule includes, for example, RNA molecules and polypeptides.

Two nucleotide sequences are considered to be "functionally homologous" if they hybridize with one another under moderately stringent conditions, i.e. 0.1% SSC at room temperature. Typically, two homologous nucleotide sequences are greater than or equal to about 60% identical when optimally aligned using the ALIGN program (Dayhoff, M. O., in ATLAS OF PROTEIN SEQUENCE AND STRUCTURE (1972) Vol. 5, National Biomedical Research Foundation, pp. 101–110, and Supplement 2 to this volume, pp. 1–10.).

Two amino acid sequences are considered "homologous" if their amino acids are greater than or equal to about 60% identical when optimally aligned using the ALIGN program mentioned above.

"Removal" in the context of a metabolite includes both physical removal as by washing and the depletion of the metabolite through the absorption and metabolizing of the metabolite by the cells.

"Signal sequence suitable to permit the heterologous protein to be secreted across the aleurone or scutellular epithelium" refers to any naturally occurring signal sequence in monocots, dicots, animals or microorganisms that can permit a protein to be secreted from the cells across the stated organs of the monocot seed. Generally, a signal sequence is a sequence of amino acids that promotes the secretion of a protein from a cell.

"Small molecules" are typically less than about 1 kilodalton and are biological, organic, or even inorganic compounds (i.e., cisplatin). Examples of such small molecules include sugars, sugar-derivatives (including phosphate derivatives), and plant hormones (such as, gibberellic or absisic acid).

"Specifically regulatable" refers to the ability of a small molecule to preferentially affect transcription from one promoter or group of promoters (e.g., the α-amylase gene family), as opposed to non-specific effects, such as, enhancement or reduction of global transcription within a cell by a small molecule.

"Substantially isolated" is used in several contexts and typically refers to the at least partial purification of a protein or polypeptide away from unrelated or contaminating components (e.g., plant proteins removed from a sample containing human α-1-antitrypsin). Methods and procedures for the isolation or purification of proteins or polypeptides are known in the art.

II. Production of Recombinant Proteins Using the Malting Process.

The invention described herein has essentially two distinct aspects. In the first aspect, the present invention relates to the discovery of the regulated expression of recombinant proteins in malted cereal seeds. Malting is the process by which grain, typically barley or rice, is germinated under controlled conditions and in contained facilities to produce a product that can be used for human consumption, animal feed and the brewing of alcoholic beverages. The process begins by steeping barley seeds in 55° F. water for 48 hours followed by a four-day germination of the grain in malting bins or drums.

During this time, the starchy portion of the seed, or endosperm, is converted to maltose and other sugars. Maltsters use water, air and, in some instances, phytohormones, like gibberellic acid, to control temperature and optimize the malting process. The malted grain is then kiln-dried at temperatures between 120° F. and 130° F. to terminate germination and remove moisture. At this point the malted grain can be stored or sold to the food, feed or brewing industries. Products of the malting process include mashes and formulated seed products. During the process of malting germinated seeds are also produced.

In the malting process, the rapid conversion of starch to sugar is accomplished by a tremendous burst of gene activity that results in the expression of a starch degrading enzyme called α-amylase. During the peak stage of germination, α-amylase is the major protein in the seed, constituting up to 60% of the total protein of the cells that surround the starchy endosperm. Alpha-amylase is secreted out of these cells and into the endosperm where it digests the starch into sugar.

Expression and secretion of α-amylase during germination is so abundant that it can be purified and sold as a research reagent for approximately $0.10 per gram. The compositions and methods described herein allow low-cost, high-volume eukaryotic production of selected gene products, such as, proteins and polypeptides, based on the malting of transgenic seeds.

This aspect of the invention includes a method of producing a protein in a monocot plant seed. Monocot plant seeds contain an endosperm surrounded by an aleurone and scutellar epithelium layer. The embryo typically begins germination and development within the endosperm. Seeds are produced, for example, from transgenic plants, that contain a chimeric gene having at least the following components:

(i) a transcriptional regulatory region inducible during seed germination, several such regions are described in detail below, including promoters from α-amylase, sucrose synthase, and sucrose-6-phosphate synthetase genes;

(ii) a heterologous first DNA sequence encoding a gene product of interest, for example, a polypeptide or protein. Exemplary DNA coding sequences are described below; and (iii) a second DNA sequence encoding signal sequence where the second DNA sequence is operably linked to the transcriptional regulatory region and the first DNA sequence. Further, the signal polypeptide sequence is (a) in translation-frame with the protein or polypeptide of interest and (b) effective to facilitate secretion of the protein or polypeptide across said aleurone or scutellar epithelium layer into the endosperm.

These seeds are malted under conditions to induce expression of the transcriptional regulatory region and production of the protein or polypeptide of interest.

The plants (including organs, seeds, tissues and cells) used in the process of the present invention are derived from monocots, particularly the members of the taxonomic family known as the Gramineae. This family includes all members of the grass family of which the edible varieties are known as cereals. The cereals include a wide variety of species such as wheat (*Triticum sps.*), rice (*Oryza, sps.*) barley (*Hordeum sps.*) oats, (*Avena sps.*) rye (*Secale sps.*), corn (*Zea sps.*) and millet (*Pennisettum sps.*).

Plant cells or tissues derived from the members of the Gramineae and are transformed with expression constructs (i.e., plasmid DNA into which the gene of interest has been inserted) using a variety of standard techniques (e.g., electroporation, protoplast fusion or microparticle bombardment). In one embodiment, the expression construct includes a transcription regulatory region (promoter) whose transcription is specifically regulated by the presence or absence of a small molecule.

In one embodiment, the gene encoding the recombinant protein is placed under the control of a metabolically regulated promoter. Metabolically regulated promoters are those in which mRNA synthesis or transcription, is repressed or induced by sugars or sugar derivatives. Examples of metabolically regulated promoters include those that transcribe some of the cereal α-amylase genes and sucrose synthase genes.

Another expression construct uses a hormonally regulated promoter to achieve expression of the recombinant protein in the germinated or malted seed. Hormonally regulated promoters are those in which mRNA synthesis or transcription, is repressed or induced by small molecules, like phytohormones such as gibberellic acid or absisic acid. Other such small molecules include, but are not limited to, indoleacetic acids, kinetins, butyric acid, oxalic acid, acetic acid, okadakic acid and arachidonic acid.

Examples of hormonally regulated promoters include those that transcribe some of the cereal α-amylase genes. The promoters relevant to this application include, but are not limited to the following: those controlling the expression of the rice (*Oryza sativa*) α-amylases genes, RAmy1A, RAmy3D and RAmy3E; the barley α-amylase gene promoter, HV18; and the sucrose synthase and sucrose-6-phosphate-synthetase (SPS) promoters from rice and barley.

Expression constructs utilize additional regulatory DNA sequences (i.e., signal peptide sequences and preferred translational start codons) to promote efficient translation and extracellular secretion of the target protein. By fusing the genes for recombinant proteins to this array of regulatory DNA sequences, the expression of recombinant proteins in germinated transgenic seeds is placed under the transcription and secretion control of a metabolically regulated or hormonally regulated promoter.

Cells or tissues or derived from cereal plants can be transformed singly or together (i.e., co-transformation) with the expression constructs. From such transformed cells transgenic plants can be regenerated. These transgenic plants are grown, allowed to produce seeds and the recombinant protein encoded by the expression construct can be recovered from malted transgenic seeds.

Figure 1B:
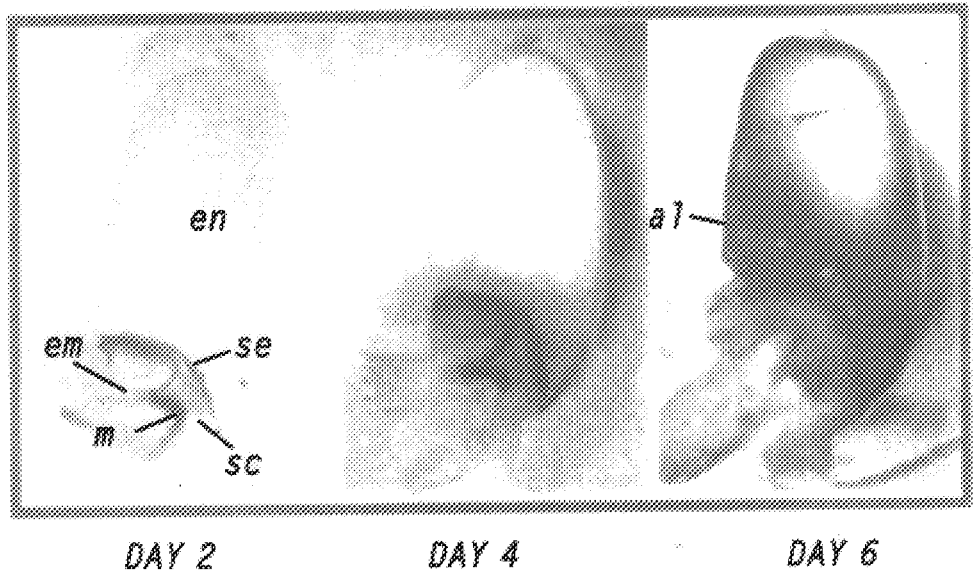
FIG. 1B is a full color photograph of the expression of the GUS gene in seed.

The principle of using different cereal α-amylase promoters to express a recombinant protein in transgenic seeds is illustrated in FIG. 1B. In this figure, the gibberellic acid-induced promoter for the RAmy1A gene, was used to express the bacterial reporter gene, gusA, in rice (Example 2). The gusA gene encodes the enzyme, beta-glucuronidase (GUS), that produces a blue chromophore in tissues expressing the gene. This chromophore can be easily detected using a histochemical staining method. In transgenic rice seeds containing the RAmy1A promoter/GUS fusion, the blue chromophore increases up to six days of germination.

Using the chimeric genes, vectors and methods of the present invention, cereal species such as rice, corn, wheat, oats, rye, barley and various grasses can be genetically engineered to express a wide range of recombinant proteins. By combining the technology of the present invention with well-established production methods (e.g., crop cultivation, malting, and product recovery), recombinant protein can be efficiently and economically produced for the biopharmaceutical, industrial processing, animal health and bioremediation industries.

The fact that this expression system does not require the use of genetic elements derived from animal or plant pathogens should facilitate regulatory acceptance.

A. Plant Expression Vectors

Expression vectors for use in the present invention comprise a chimeric gene (or expression cassette), designed for operation in plants, with companion sequences upstream and downstream from the expression cassette. The companion sequences will be of plasmid or viral origin and provide necessary characteristics to the vector to permit the vectors to move DNA from bacteria to the desired plant host.

The basic bacterial/plant vector construct will preferably provide a broad host range prokaryote replication origin; a prokaryote selectable marker; and, for Agrobacterium transformations, T DNA sequences for Agrobacterium-mediated transfer to plant chromosomes. Where the heterologous gene is not readily amenable to detection, the construct will preferably also have a selectable marker gene suitable for determining if a plant cell has been transformed. A general review of suitable markers for the members of the grass family is found in Wilmink and Dons, 1993, *Plant Mol. Biol. Reptr*, 11(2):165–185.

Sequences suitable for permitting integration of the heterologous sequence into the plant genome are also recommended. These might include transposon sequences, and the like, for homologous recombination, as well as Ti sequences which permit random insertion of a heterologous expression cassette into a plant genome.

Suitable prokaryote selectable markers include resistance toward antibiotics such as ampicillin or tetracycline. Other DNA sequences encoding additional functions may also be present in the vector, as is known in the art.

The constructs of the subject invention will include the expression cassette for expression of the protein(s) of interest. Usually, there will be only one expression cassette, although two or more are feasible. The recombinant expression cassette contains, in addition to the heterologous protein encoding sequence, at least the following elements: a promoter region, plant 5' untranslated sequences, initiation codon depending upon whether or not the structural gene comes equipped with one, and transcription and translation termination sequences. Unique restriction enzyme sites at the 5' and 3' ends of the cassette allow for easy insertion into a pre-existing vector. These elements are discussed in detail below.

1. Heterologous Coding Sequences.

The heterologous coding sequence may be for any protein of interest, either prokaryotic or eukaryotic, particularly eukaryotic. The gene providing the desired product will particularly be those genes associated with large volume products. Therefore, products of particular interest include but are not limited to enzymes, such as chymosin, proteases, polymerases, saccharidases, dehydrogenases, nucleases, glucanase, glucose oxidase, α-amylase, oxidoreductases (such as fungal peroxidases and laccases), xylanases, phytase, cellulase, hemicellulase, and lipase. More specifically, the invention can be used to produce enzymes such as those used in detergents, rennin, horse radish peroxidase, amylases from other plants, soil remediation enzymes, and other such industrial proteins.

Other proteins of interest are mammalian proteins. Such proteins include, but are not limited to blood proteins (such as, serum albumin, Factor VII, Factor VIII (or modified Factor VIII), Factor IX, Factor X, tissue plasminogen factor, Protein C, von Willebrand factor, antithrombin III, and erythropoietin), colony stimulating factors (such as, granulocyte colony-stimulating factor (G-CSF), macrophage colony-stimulating factor (M-CSF), and granulocyte macrophage colony-stimulating factor (GM-CSF)), cytokines (such as, interleukins), integrins, addressins, selectins, homing receptors, surface membrane proteins (such as, surface membrane protein receptors), T cell receptor units, immunoglobulins, soluble major histocompatibility complex antigens, structural proteins (such as, collagen, fibroin, elastin, tubulin, actin, and myosin), growth factor receptors, growth factors, growth hormone, cell cycle proteins, vaccines, fibrinogen, thrombin, cytokines, hyaluronic acid and antibodies.

While for the most part, the product will be a peptidic product, genes may be introduced which may serve to modify non-peptidic products produced by the cells. These proteins, fragments thereof, usually of at least about 30 amino acids, fused combinations, mutants, and synthetic proteins, whether the proteins may be synthetic in whole or in part, so far as their sequence in relation to a natural protein, may be produced.

The present invention also provides the advantage that polypeptide useful for veterinary use, such as, vaccines and growth hormones, may be produced by the malting process of the present invention. The products of the malting reaction, containing the polypeptide of interest, can then be formulated into mash product or formulated seed product directly useful in veterinary applications.

2. Signal Sequences

Also included in chimeric genes used in the practice of the method of the present invention are signal secretion sequences. In addition to encoding the protein of interest, the chimeric gene also encodes a signal peptide that allows processing and translocation of the protein, as appropriate. The chimeric gene typically lacks any sequence that might result in the binding of the desired protein to a membrane.

Typically, the transcriptional regulatory region (i.e., the transcription initiating region) is derived from a gene whose product is expressed and translocated during germination. By employing the signal peptide homologous to such a transcriptional regulatory region, translocation of the protein of interest is achieved. In this way, the protein(s) of interest are translocated from the cells in which they are expressed and may be efficiently harvested.

While it is not required that the protein be secreted from the cells in which the protein is produced, this facilitates the isolation and purification of the recombinant protein. Table 1 provides a list of known signal sequences from wheat, barley and rice. Typically, these signal sequences facilitate secretion of proteins expressed in seeds across the aleurone or scutellar epithelium layer into the endosperm of the seed.

TABLE 1

Signal peptides of α-amylase genes
B-, barley α-amylase genes. W-, wheat α-amylase genes;
, signal peptide cleavage site determined by protein sequencing;
*, predicted signal peptide cleavage site; /, intron splice site;
".", space inserted to maximize the alignment.

| Genes | References |
|---|---|
| RAmy1A | Plant Molecular Biology. 14:655–668 (1990). |
| RAmy1B | Nucleic Acids Research. 18:7007–7014 (1990). |
| aAmy10-c | Gene. 122:247–253 (1992). |
| W-Amy1/13 Mol. | Gen. Genet. 209:33–40 (1987). |
| W-2128 | Gene. 55:353–356 (1987). |
| B-pM/C | Plant Molecular Biology. 3:407–418 (1984) and Journal of Biological Chemistry. 260:3731–3738 (1985). |
| B-gKAmy141 | Plant Molecular Biology. 9:3–17 (1987). |
| RAmy2A | Gene. 111:223–228 (1992). |
| W-Amy2/54 | Mol. Gen. Genet. 209:33–40 (1987). |
| B-clone E | Plant Molecular Biology. 3:407–418 (1984) and J. of Biological Chemistry 260:3731–3738 (1985). |
| B-gKAmy155 | Plant Molecular Biology. 3:407–418 (1984) and Plant Molecular Biology. 9:3–17 (1987). |
| B-Amy32b | Plant Molecular Biology. 3:407–418 (1984) and Nucleic Acids Research 15:2515–2535 (1987). |
| RAmy3A | Plant Molecular Biology. 16:579–591 (1991). |

TABLE 1-continued

Signal peptides of α-amylase genes
B-, barley α-amylase genes. W-, wheat α-amylase genes;
, signal peptide cleavage site determined by protein sequencing;
*, predicted signal peptide cleavage site; /, intron splice site;
".", space inserted to maximize the alignment.

| Genes | References |
|---|---|
| RAmy3B | Plant Molecular Biology. 16:579–591 (1991). |
| RAmy3C | Plant Molecular Biology. 16:579–591 (1991). |
| RAmy3D | Nucleic Acids Research. 18:7007–7014 (1990). |
| RAmy3E | Nucleic Acids Research. 18:7007–7014 (1990). |
| W-Amy3/33 | Mol. Gen. Genet. 209:33–40 (1987). |
| Taka-amylase | Molecular Microbiology. 3:3–14 (1989). |

Those of skill can routinely identify new signal peptides. Plant signal peptides typically have a tripartite structure, with positively-charged amino acids at the N-terminal end, followed by a hydrophobic region and then the cleavage site within a region of reduced hydrophobicity. The conservation of this mechanism is demonstrated by the fact that cereal α-amylase signal peptides are recognized and cleaved in foreign hosts such as E. coli and S. cerevisiae.

The flexibility of this mechanism is reflected in the wide range of polypeptide sequences that can serve as signal peptides. Thus, the ability of a sequence to function as a signal peptide may not be evident from casual inspection of the amino acid sequence. Methods designed to predict signal peptide cleavage sites identify the correct site for only about 75% of the sequences analyzed. (See Heijne Gv: Cleavage-site motifs in protein targeting sequences. In: J. K. Setlow (eds) Genetic Engineering, Vol. 14. Plenum Press, New York (1992)).

Although, sequence homology is not always present in the signal peptides, hydrophilicity plots demonstrate that the signal peptides of these genes are relatively hydrophobic.

3. Promoters (a) Exemplary Transcription Regulatory Regions

The preferred transcription regulatory or promoter region is chosen so as to be relatively silent, except during seed germination. For example, the expression level in the seed cells is at least about 20 times the expression level in other plant tissue during the growth of the plant. This type of transcriptional regulation can be achieved in various ways, including the following: (i) by using the 5'-non-coding region associated with a protein which is produced solely or substantially solely during seed germination, or (ii) by using the regulatory portion of such a transcriptional initiation region in conjunction with a different RNA polymerase binding region.

In referring to a "substantial absence of expression" at times other than seed germination, it is intended that expression be very low or non-existent except during seed germination. That is, the expression of the protein of interest, encoded by the chimeric gene, is low so as (i) to not affect the growth of the plant or expend significant plant resources, (ii) to not diminish the vigor of the plant growth, and (iii) to allow for the plant and mash to be used for its intended purpose, depending on the protein of interest.

A number of proteins are normally secreted across either the aleurone or scutellum during seed germination and seed elongation. Some examples of secreted plant enzymes induced by gibberellic acid include, but are not limited to the following: α-amylase, protease, ribonuclease, β-glucanase, esterase, acid phosphatases (such as p-nitrophenyl, phosphatase, ATPase, phytase, naphthol AS-B1 phosphatase, and GTPase), pentosanase, endoxylanase, xylopyranosidase, arabinofuranosidase, glucosidase, and peroxidase.

In view of the teachings of the present specification, one of skill in the art can recognize and implement useful promoter/signal sequence combinations for the practice of the present invention. Because many of the useful sequences are evolutionarily related, the conserved sequences facilitate the identification of new promoters and signal sequences useful in the practice of this invention.

Standard nucleic acid hybridization technology can be used to probe libraries of other monocots, using previously identified promoters and signal sequences, to identify "homologs" in these monocots. For example, a gene having a promoter region of interest is selected, a probe specifically hybridizable to the gene is chosen, and traditional cross-hybridization experiments are performed under varying solution stringencies. This method has been employed using the rice RAmy1A as a probe to identify a homolog promoter in barley; the barley promoter for HV18 (SEQ ID NO:1).

Polymerase chain reaction technology (PCR; Mullis, K. B., U.S. Pat. No. 4,683,202, issued 28 Jul. 1987; Mullis, K. B., et al., U.S. Pat. No. 4,683,195, issued 28 Jul. 1987) can also be used to identify homologs of known promoters, for example, amplify unknown promoter using PCR primers able to bind to conserved regions of a selected promoter or signal sequence. Examples of conserved sequences in the rice amylase promoter regions are provided in Table 2. The sequences for the rice promoters were reported in Huang N., et al., 1990, Nucl. Acids Res. 18:7007–7014 (1990) and the taka promoter from Aspergillus oryzae was reported in Wirsel, 1989, Molecular Microbiology, 3:3–14.

TABLE 2

Conserved sequences in the RAmy3D, RAmy3E and Take-amylase promoters

| 31 bp RAmy3D | GAGACCGGGCCCCGACGCGGCCGACGCGGCG<br>++++ + ++ +++ + ++ ++ +++++++ | SEQ ID NO: 3 |
|---|---|---|
| 31 bp RAmy3E | GAGAGCTCGCGCCGCCTCGATCGGCGCGGCG | SEQ ID NO: 4 |
| 11 bp RAmy3D | TTCCGGCTTGC<br>++ ++++++++ | SEQ ID NO: 5 |
| 11 bp RAmy3E | TTGCGGCTTGC | SEQ ID NO: 6 |
| Taka-amylase | CGGCCCGTCGGC | SEQ ID NO: 7 |

The "+" symbols indicate positions at which the RAmy3D and RAmy3E sequences are identical.

The situation in rice is demonstrative. In rice, the α-amylase isozymes are encoded by a family of nine genes (Table 3). They are referred to as RAmy1A, 1B, 1C, 2A, 3A, 3B, 3C, 3D and 3E. The Rice α-Amylase genes are classified into three subfamilies (RAmy1, RAmy2, and RAmy3) (See Huang, et al., 1992, *Proc. Natl. Acad. Sci. USA*. 89:7526–7530 and Huang N, et al., 1990, *Plant Molecular Biology*, 14:655–668) based on DNA sequence similarities to α-amylase gene subfamilies in other cereal species. Eight members of the α-amylase gene family in rice have been isolated and characterized. A partial cDNA sequence, presumably corresponding to RAmy1C, has been reported in Yu S-M, et al., 1992, *Gene*. 122:247–253. The α-amylase genes have been mapped to five different chromosomes in rice.

TABLE 3

Alpha-amylase gene expression in rice tissues

| Gene Names | Germinated Seedlings | Root | Leaf | Developing Seeds | Cultured Cells |
|---|---|---|---|---|---|
| All Genes | 100[a] | 1 | 3 | 4 | 65 |
| RAmy1A | ++++[b] | ++++ | ++++ | +++ | ++ |
| RAmy1B | − | − | − | − | + |
| RAmy1C | −[c] | NA[d] | NA | NA | NA |
| RAmy2A | + | + | + | + | + |
| RAmy3A | + | − | − | − | ++ |
| Ramy3B | ++ | NA | NA | NA | NA |
| RAmy3C | ++ | NA | NA | NA | NA |
| RAmy3D | ++ | ++ | ++ | − | ++++ |
| RAmy3E | +++ | +++ | +++ | ++++ | +++ |

[a]Relative mRNA levels for all α-amylase genes are normalized to the level of expression observed in germinated seedlings by Northern blot hybridization.
[b]Relative levels of mRNA for each gene as estimated from Northern blot hybridization or RNA-PCR experiments. The amount of PCR product is indicated from the highest (++++) to the lowest (+). Minus signs (−) indicate that no product was observed in the RNA-PCR reaction.
[c]Lack of expression based on restriction digest of RNA-PCR products.
[d]NA = Not Available Embodiments of the present invention include promoter/signal sequence combinations of RAmy 1A, 3D and 3E, where expression is at a high level during germination. The 5'-non-coding region of 3E is characterized by a region conserved with 3D, which is a GC-rich sequence of 31 bases and contains two CGGC repeats. There is also an 11 base sequence which is conserved which contains a single copy of the CGGC sequence.

The 3D and 3E α-amylase genes are subject to suppression of expression by sugars, particularly sucrose, glucose, fructose, and maltose. Thus, during cell fermentation, premature expression of the desired product can be avoided by employing a sugar, particularly, sucrose, in the growth medium. Thus, sucrose may be used as a carbon source by the cells and, when the sucrose is exhausted, expression of the desired proteins will be initiated.

Other transcription initiation regulatory regions that may be employed include those that are induced by sugar such as sucrose synthase.

Complex transcriptional initiation regions can be employed by using the regulatory portion of one transcriptional initiation region with the RNA polymerase binding region of a different gene. In this way, expression can be regulated while providing for a high level of expression.

A preferred embodiment of the present invention uses a promoter that is regulated during germination. For example, the hormones absisics acid (ABA) and gibberellic acid (GA) play important regulatory roles in control of α-amylase gene expression in cereal seeds. ABA, which is synthesized during grain filling, acts as a negative regulator of transcription for α-amylase and many other genes. ABA levels drop in the mature desiccated grain, thus relieving the inhibition of α-amylase and other genes required for germination.

Obviously up-regulation is desired for over expression of heterologous proteins and GA mediated promoters are a desired embodiment. The prevailing model for GA regulation during cereal seedling development involves the diffusion of GA from the embryo to the aleurone layer. GA then induces the synthesis of hydrolytic enzymes such as α-amylase. In rice, GA stimulates α-amylase gene expression in aleurone tissues.

But not all α-amylase promoters are induced by GA and not all are inducible when present in undifferentiated cells, such as those used in culture or when removed from the intact seed. For example RAmy3D and RAmy3E in rice callus and cultured cells are unaffected by GA. No significant change in levels of RAmy3D and RAmy3E expression was detected in rice callus treated with GA and there are reports that callus treated with paclobutrazol, an inhibitor of gibberellin biosynthesis, produced the same amount of α-amylase protein as untreated callus.

Finally, callus cultures derived from seeds of the GA-deficient dwarf mutant, cv. Tan-ginbozu, produced the same levels of α-amylase gene expression with or without exogenous GA treatment. This suggests that Ramy3D and Ramy3E gene expression in the scutellum and in cultured cells is independent of GA regulation.

The GA independent promoters appear to be missing a short sequence that is present in GA inducible promoters. DNA sequence comparisons have identified four short, conserved sequences in the cereal α-amylase promoters. The TATA Box (CTATAAATAG) is the binding site required for RNA polymerase II to initiate transcription. The Pyrimidine Box (YCTTTTY) and Box I (TATCCAT) may be involved in the developmental regulation of the genes in the scutellum and aleurone.

The GARE Box (GA-Responsive Element) (TAACRRA) is required for GA-induction and ABA-repression of α-amylase gene expression. The GARE Box (GA-Responsive Element) in the RAmy1A gene (genomic clone lOSg2) is located at base-143 relative to the transcription start site. Expression of the RAmy1A gene (cDNA clone pOS103) is stimulated 50–100 fold by exogenous GA. The absence of GARE Box sequences in the promoters of the rice RAmy3D and RAmy3E genes is consistent with the GA-independent expression of these genes as discussed above.

Alternatively the agent inducing expression can be a metabolite which is either a sugar or phosphorylated sugar. For example, RAmy3D gene expression is metabolically regulated in rice embryo tissues. Evidence for this is based on studies in which seeds were moistened to initiate seedling development and harvested after 0 to 48 hours of incubation. Embryos dissected out of these seeds had low levels of expression for RAmy3D. This pattern of expression was reversed if embryos were first removed from the seed at time zero and incubated in water for 0 to 48 hours. Under these conditions, RAmy3D expression increased to five times the level observed in the intact rice seed.

Addition of sugar to the incubation medium used for the isolated embryos restored normal expression of the RAmy3D gene (see examples). A number of sugars, including sucrose, glucose, fructose and maltose, were able to repress RAmy3D gene expression in isolated embryos (Karrer and Rodriguez, 1992, *The Plant Journal*, 2:517–523).

In rice cell suspension cultures, α-amylase enzyme activity increases after the depletion of sucrose from the medium. This increase is consistent with the pattern of α-amylase mRNA accumulation, which also increases dramatically after the culture medium is depleted of sugar. Cells transferred to sugar-free medium begin to produce elevated levels of total α-amylase mRNA within four hours. (See Yu S-M, et al., 1991, *J Biol. Chem.* 266:21131–21137 (1991).

Dot blot hybridization and gene-specific probes have been used to demonstrate that sugar controls the expression of both RAmy3D and RAmy3E in cultured cells. Cells were subcultured into medium with 1%, 3%, 6% or 12% sucrose. RNA isolated from cells cultured for five days showed that RAmy3D and RAmy3E expression was repressed at the higher sugar concentrations. Expression of both of these genes was induced in the cells cultured in 1% sucrose, presumably after sugar was depleted from the medium by cell growth. Expression of the RAmy1A and RAmy3A genes was unaffected by these treatments. Thus, expression of the RAmy3D and RAmy3E genes is metabolically regulated by the concentration of sugar in the culture medium.

To confirm that this regulation is acting at the level of transcription, the RAmy3D promoter was linked to the GUS reporter gene. The amount of GUS enzyme activity produced by the cells provides a convenient measure of the expression of the engineered RAmy3D promoter. The RAmy3D promoter/GUS gene construct was co-electroporated into protoplasts with another plasmid containing the gene for hygromycin-resistance. Southern blot hybridization showed that hygromycin-resistant cell lines contained the RAmy3D/GUS gene construct. GUS activity was reduced in transformed cell lines grown at elevated sucrose concentrations (see examples). GUS activity increased starting eight hours after the cells were transferred to sugar-free medium. These data demonstrate that the GUS reporter gene is being regulated by the RAmy3D promoter in cell culture just as the endogenous RAmy3D gene is regulated in the rice seed.

The promoters of the RAmy3D and RAmy3E genes have little sequence similarity, but there are two conserved sequences in their promoters that may be involved in the metabolic regulation of these genes. A GC-rich sequence of 31 bases in RAmy3D (Table 2) contains two CGGC repeats (underlined). This tandem repeat structure within the 31 base sequence is similar to the DNA binding sites for Spl, a mammalian transcription regulatory protein.

An eleven-base sequence (Table 2), which is conserved in both the RAmy3D and the RAmy3E promoter, contains a single copy of the CGGC sequence. A tandem duplication of the CGGC sequence is also found in the promoters of the Taka-amylase genes of Aspergillus oryzae. These CGGC sequences are found in the 87 base region of the Taka-amylase promoters (from position −377 to −290) that has been implicated in the metabolic regulation of these genes.

(b) General Sources of Promoter and Signal Sequences

In view of the guidance of the present disclosure and by using a number of standard procedures, one of skill can identify suitable promoters and signal sequences in addition to those described above for use in this invention. While the gene can be amplified directly from a mRNA extract using PCR, the first step is generally to produce a genomic or cDNA library.

In brief, genomic or cDNA libraries are prepared according to standard techniques as described, for instance, in Sambrook, et al., *Molecular Cloning—A Laboratory Manual*, Cold spring Harbor Laboratory, Cold Spring Harbor, N.Y. 1989. To construct genomic libraries, large segments of genomic DNA are generated by random fragmentation and are ligated with vector DNA to form concatemers that can be packaged into the appropriate vector. Two kinds of vectors are commonly used for this purpose, bacteriophage lambda vectors and cosmids. Alternatively, genomic libraries can be purchased from commercial sources (e.g., Clontech, Palo Alto, Calif.).

In the present invention, cDNA libraries enriched, for example, for α-amylase secreting mRNA sequences are used to screen for the desired genes. Preparation of appropriately enriched cDNA would involve the use of plant organs over expressing and secreting α-amylase, e.g., aleurone layers. Other organs would include roots, stems, leaves and panicles. Briefly, mRNA from select tissue is isolated and cDNA is prepared. Short chains of oligo d-T nucleotides are hybridized with the poly-A tails of the mRNA and serve as a primer for the enzyme, reverse transcriptase, which synthesizes a complementary DNA (cDNA) strand.

The cDNA can be optionally enriched for the desired sequences using subtraction hybridization procedures by labelling the cDNA and hybridizing it with mRNA from tissue that does not express the desired mRNA according to the procedures. *Proc. Natl. Acad. Sci. U.S.A.* 81:2194–2198 (1984).

Unreacted cDNA is isolated and used to prepare a library for screening. To do this, a second DNA strand is synthesized using the first cDNA strand as a template. Linkers are added to the double-stranded cDNA for insertion into a plasmid or λ phage vector for propagation in *E. coli*.

Identification of clones harboring the desired sequences is performed by either nucleic acid hybridization or immunological detection of the encoded protein, if an expression vector is used. Typically, oligonucleotide probes specific for the gene of interest are used.

After identification of a cDNA corresponding to the gene of interest, the cDNA molecule can be used as a probe of a genomic DNA, containing the gene of interest. Corresponding genomic clones are identified. Genomic clones isolated with this approach will contain gene sequences that include the promoter, coding region, introns and terminators.

Alternatively, the probes specific to the gene of interest can be used to directly probe genomic DNA libraries from a selected plant. Sequences homologous to the probe can be isolated by standard techniques, including hybridization screening or polymerase chain reaction.

Oligonucleotide and cDNA probes useful for identification of other promoters and signal sequences can also be prepared from conserved regions of related genes in other species. By comparing the nucleotide sequences of the known proteins, one simply identifies conserved sequences in the genes and uses those sequences as probes or as PCR primers to locate homologous sequences in genomic or cDNA libraries of other plants. A number of references compare regions of nucleotide homology and amino acid identity regarding secreting genes and they are provided below. Such conserved sequences can be used to isolate other genes having a hormonal or other metabolite responsive promoter.

Probes, typically used to identify related but heretofore unknown target sequences, can be hybridized under stringent conditions to ensure that the sequences are in fact related. Typically, stringent conditions suitable for finding related sequences would be performing the hybridization at a melting temperature (Tm) of between −15° C. to −20° C.

(c) Cloning of the Desired DNA Sequences

Once the DNA encoding the desired sequences has been located, sufficient quantity of the gene must be generated to facilitate subsequent recombinant manipulations. Although the sequences can be directly amplified by PCR, they are most commonly replicated in an intermediate bacterial host. Most commonly in a bacteria of the genera Escherichia, Bacillus and Streptomyces. Cloning for amplification of intermediate vectors is most preferred in *E. coli* because that organism is easy to culture and more fully understood than other species of prokaryotes.

Sambrook, supra, contains methodology sufficient to conduct clonings in *E. coli*. Strain HB101 is a useful strain which is typically grown on Luria broth (LB) with glucose, Difco's Antibiotic Medium #2 and M9 medium supplemented with glucose and acid-hydrolyzed casein amino acids. Strains with resistance to antibiotics are maintained at the drug concentrations described in Sambrook, supra.

Transformations are performed according to the method described by Morrison, D. A. (1977), *J. Bacteriol.*, 132:349–351; or by Clark-Curtiss, J. E. and Curtiss, R., 1983, in *Methods in Enzymology*, 101:347–362, Wu, R., Grossman, L. and Moldave, K., eds., Academic Press, New York. Representative vectors include pBR322 and the pUC series which are available from commercial sources.

4. Transcription and Translation Terminators

The expression cassettes or chimeric genes of the present invention typically have a transcriptional termination region at the opposite end from the transcription initiation regulatory region. The transcriptional termination region may normally be associated with the transcriptional initiation region or from a different gene. The transcriptional termination region may be selected, particularly for stability of the mRNA to enhance expression. Illustrative transcriptional termination regions include the NOS terminator from Agrobacterium Ti plasmid and the rice α-amylase terminator.

Polyadenylation tails, Alber and Kawasaki, 1982, *Mol. and Appl. Genet.* 1:419–434 are also commonly added to the expression cassette to optimize high levels of transcription and proper transcription termination, respectively. Polyadenylation sequences include but are not limited to the Agrobacterium octopine synthetase signal, Gielen, et al., *EMBO J.* 3:835–846, 1984 or the nopaline synthase of the same species Depicker, et al., *Mol. Appl. Genet.* 1:561–573, 1982.

Since the ultimate expression of the desired gene product will be in a eukaryotic cell (e.g., a member of the grass family), it is desirable to determine whether any portion of the cloned gene contains sequences which will be processed out as introns by the host's splicosome machinery. If so, site-directed mutagenesis of the "intron" region may be conducted to prevent losing a portion of the genetic message as a false intron code, Reed and Maniatis, Cell 41:95–105, 1985.

5. Transformation of Plant Cells (a) Direct Transformation

Vectors containing a chimeric gene of the present invention can introduced into plant cells by a variety of techniques. These vectors may include selectable markers for use in plant cells (such as, the nptII kanamycin resistance gene). The vectors may also include sequences that allow their selection and propagation in a secondary host, such as, sequences containing an origin of replication and a selectable marker. Typical secondary hosts include bacteria and yeast. In one embodiment, the secondary host is *Escherichia coli*, the origin of replication is a colE1-type, and the selectable marker is a gene encoding ampicillin resistance. Such sequences are well known in the art and are commercially available as well (e.g., Clontech, Palo Alto, Calif.; Stratagene, La Jolla, Calif.).

The vectors of the present invention may also be modified to intermediate plant transformation plasmids that contain a region of homology to an *Agrobacterium tumefaciens* vector, a T-DNA border region from *Agrobacterium tumefaciens*, and chimeric genes or expression cassettes (described above). Further, the vectors of the invention may comprise a disarmed plant tumor inducing plasmid of *Agrobacterium tumefaciens*.

Vectors useful in the practice of the present invention may be microinjected directly into plant cells by use of micropipettes to mechanically transfer the recombinant DNA. Crossway, *Mol. Gen. Genet*, 202:179–185, 1985. The genetic material may also be transferred into the plant c/ell by using polyethylene glycol, Krens, et al., *Nature*, 296, 72–74, 1982.

Another method of introduction of nucleic acid segments is high velocity ballistic penetration by small particles with the nucleic acid either within the matrix of small beads or particles, or on the surface, Klein, et al., *Nature*, 327, 70–73, 1987 and Knudsen and Muller, 1991, *Planta*, 185:330–336 (teaching particle bombardment of barley endosperm to create transgenic barley).

Yet another method of introduction would be fusion of protoplasts with other entities, either minicells, cells, lysosomes or other fusible lipid-surfaced bodies, Fraley, et al., *Proc. Natl. Acad. Sci. USA*, 79, 1859–1863, 1982.

The vector may also be introduced into the plant cells by electroporation. (From, et al., *Pro. Natl Acad. Sci. USA* 82:5824, 1985). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

(b) Vectored Transformation

A common vector method of introducing the vector into plant cells is to infect a plant cell with *Agrobacterium tumefaciens* previously transformed with the gene. Under appropriate conditions known in the art, the transformed plant cells are grown to form shoots or roots, and develop further into plants.

Agrobacterium a representative genus of the gram-negative family Rhizobiaceae. Its species are responsible for plant tumors such as crown gall and hairy root disease. In the dedifferentiated tissue characteristic of the tumors, amino acid derivatives known as opines are produced and catabolized. The bacterial genes responsible for expression of opines are a convenient source of control elements for chimeric expression cassettes.

Heterologous genetic sequences, such as the chimeric genes of the present invention, can be introduced into appropriate plant cells, by means of the Ti plasmid of *Agrobacterium tumefaciens*. The Ti plasmid is transmitted to plant cells on infection by *Agrobacterium tumefaciens*, and is stably integrated into the plant genome. J. Schell, *Science* 237: 1176–1183, 1987.

Ti plasmids contain two regions essential for the production of transformed cells. One of these, named transferred DNA (T-DNA), is transferred to plant nuclei and induces tumor formation. The other, termed virulence region, is essential for the transfer of this T-DNA but is not itself transferred. The transferred DNA region, which transfers to the plant genome, can be increased in size by the insertion of the gene encoding group 3 LEA proteins without its ability to be transferred being affected.

A modified Ti plasmid, in which the tumor-causing genes have been deleted, can be used as a vector for the transfer of the gene constructs of this invention into an appropriate plant cell.

Construction of recombinant Ti plasmids in general follows methods typically used with the more common bacterial vectors such as pBR322. Additional use can be made of accessory genetic elements sometimes found with the native plasmids and sometimes constructed from foreign sequences. These may include but are not limited to "shuttle vectors", Ruvkun and Ausubel, 1981, *Nature* 298:85–88, promoters, Lawton, et al., 1987, *Plant Mol. Biol.* 9:315–324 and structural genes for antibiotic resistance as a selection factor, Fraley, et al., *Proc. Natl. Acad. Sci.* 80:4803–4807, 1983.

Species which are a natural plant host for Agrobacterium may be transformable in vitro. Monocotyledonous plants, and in particular, cereals and grasses, are not natural hosts to Agrobacterium. Attempts to transform them using Agrobacterium have been unsuccessful until recently. Hooykas-Van Slogteren, et al., *Nature* 311:763–764, 1984. There is growing evidence now that certain monocots can be transformed by Agrobacterium. Using novel experimental approaches that have now become available, cereal and grass species may now be transformed.

Promoters directing expression of selectable markers used for plant transformation (e.g., nptII) should operate effectively in plant hosts. One such promoter is the nos promoter from native Ti plasmids, Herrera-Estrella, et al., *Nature* 303:209–213, 1983. Others include the 35S and 19S promoters of cauliflower mosaic virus, Odell, et al., *Nature* 313:810–812, 1985, and the 2' promoter, Velten, et al., *EMBO J.* 3, 2723–2730, 1984.

6. Plant Regeneration

After determination of the presence and expression of the desired gene products, whole plant regeneration is desired. Plant regeneration from cultured protoplasts is described in Evans, et al., *Handbook of Plant Cell Cultures*, Vol. 1: (MacMillan Publishing Co. New York, 1983); and Vasil I. R. (ed.), *Cell Culture and Somatic Cell Genetics of Plants*, Acad. Press, Orlando, Vol. I, 1984, and Vol. III, 1986.

All plants from which protoplasts can be isolated and cultured to give whole regenerated plants can be transformed by the present invention so that whole plants are recovered which contain the transferred gene. It is known that practically all plants can be regenerated from cultured cells or tissues, including but not limited to all major species of sugarcane, sugar beet, cotton, fruit and other trees, legumes and vegetables, and monocots.

Some suitable plants include, for example, species of wheat, rice, oats, rye, corn, sorghum, millet and barley.

Means for regeneration vary from species to species of plants, but generally a suspension of transformed protoplasts containing copies of the heterologous gene is first provided. Callus tissue is formed and shoots may be induced from callus and subsequently rooted.

Alternatively, embryo formation can be induced from the protoplast suspension. These embryos germinate as natural embryos to form plants. The culture media will generally contain various amino acids and hormones, such as auxin and cytokinins. It is also advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

The mature plants, grown from the transformed plant cells, are selfed and non-segregating, homozygous transgenic plants are identified. The inbred plant produces seed containing the chimeric gene of the present invention. These seeds can be malted to produce the protein or polypeptide of interest.

The inbreds according to this invention can be used to develop hybrids or novel varieties embodying the desired traits. Such plants would be developed using traditional selection type breeding.

The transgenic seeds produced by the method of the present invention can be formed into seed products.

B. Antisense Applications

In addition to the above indicated genes, one may also have constructs which provide for inactivation of endogenously expressed genes. Of particular interest is the inactivation of genes that are expressed during germination and seedling elongation. These genes may include one or more of the amylases, e.g., RAmy3B, RAmy3C, RAmy3E or homologs thereof.

Inactivation of gene expression may be achieved in a number of ways. The most convenient is the use of an anti-sense sequence, where the anti-sense sequence may be complementary to any portion of the mRNA, including both the non-coding and coding regions. Normally, the anti-sense sequence will be at least about 30 nt, more usually at least about 50 nt, and may be up to or greater than the sequence of the mRNA to which the anti-sense sequence is complementary.

In one embodiment, the 3'-terminal sequence of the anti-sense sequence is selected to provide for mRNA stability, there being a number of sequences which are known to destabilize the mRNA which can be avoided.

The transcription initiation region for the anti-sense sequence may be constitutive or inducible. A relatively strong promoter may be employed, such as, the 35S CMV promotor, the RUBSICO promoter, or beta-conglycinin promoter. Preferably, the transcription initiation region is inducible so as to be induced during the malting process. To enhance the transcription of the anti-sense sequence, one may use various enhancers associated with other promoters to increase the rate of transcription of the anti-sense sequence.

It is not necessary that all expression of one or more proteins naturally produced during malting is inhibited, it being sufficient that there be at least about a 10%, preferably at least about a 25% reduction in expression, so as to increase the proportion of the desired protein in the malting product. Enhancers which find use include the 35S CMV enhancer, and the introns of the alcohol dehydrogenase gene of maize.

III. The Malting Process

The malting process is a multi-step process. The first step is steeping. During steeping seed is immersed in or sprayed with water to increase the moisture content of the seed to between 35–45%. This initiates germination. Steeping typically takes place in a steep tank which is typically fitted with a conical end to allow the seed to flow freely out. The addition of compressed air to oxygenate the steeping process is an option. The temperature is controlled at approximately 22° C. depending on the seed.

After steeping, the seed is transferred to germination compartments. The seed is either wet or dry transferred. The germination bin contains air saturated with water and is under controlled temperature and air flows. The typical temperatures are between 12°–25° C. and germination is permitted to continue for from 3 to 7 days.

Where the heterologous protein is operably linked to a inducible promoter requiring a metabolite such as sugar or plant hormone, this metabolite is added, removed or depleted from the steeping water medium and/or is added to the water saturated air used during germination. The seed absorbs the aqueous medium and begins to germinate expressing the heterologous protein. The medium may then be withdrawn and the malting begun, by maintaining the seeds in a moist temperature controlled aerated environment. In this way, the seeds may begin growth prior to expression, so that the expressed product is less likely to be partially degraded or denatured during the process. Other components included in the imbibition medium may be plant hormones, such as gibberellic acid, generally in an amount from about 2.5 to 100 μM.

Where the promoter is induced by sugar, glucose or sucrose can be added to the imbibition media during steeping or during germination. The sugar concentration may range up to about 12 weight percent of the medium.

More specifically, the temperature during the imbibition or steeping phase will be maintained in the range of about 15°–25° C., while the temperature during the germination will usually be about 20° C. The time for the imbibition will usually be from about 2 to 4 days, while the germination time will usually be an additional 2 to 10 days, more usually 3 to 7 days. Usually, the time for the malting does not exceed about ten days. The period for the malting can be reduced by using plant hormones during the imbibition, particularly gibberellic acid.

Germinated seed produced by this method may be used to produce germinated seed products.

To achieve maximum production of recombinant protein from malting, the malting procedure will be modified to accommodate de-hulled and de-embryonated seeds. The hulls and embryos are dehulled and de-embryonated using standard means which include rollers, other mechanical means of breaking the intact embryos free of hull and endosperm. Screening is typically used to separate the embryos from unwanted seed debris. Isolated transgenic embryos are germinated in steeping water containing $CaCl_2$ (approx 10 mM).

In the absence of sugars from the endosperm, there is expected to be a 5 to 10 fold increase in RAmy3D promoter activity and thus expression of the heterologous protein. Alternatively when embryoless-half seeds are incubated in 10 mM $CaCl_2$ and 5 μm gibberellic acid, there is a 50 fold increase in RAmy1A promoter activity.

In this system, recombinant proteins under the control of RAmy1A (HV18 or other homologs) and RAmy3D promoters are secreted into the medium. Specialized malting bins or steep tanks may be used. The embryos and embryoless-half seeds are mechanically disrupted to release any secreted protein between cells and tissues. The mixture is suspended in a buffer solution to retrieve soluble proteins. Conventional protein isolation and purification methods are then used to purify the recombinant protein. Parameters of time, temperature pH, oxygen, and volumes are adjusted through routine methods to optimize expression and recovery of heterologous protein.

An optional step is kilning the germinated seed. Kilning is a low temperature drying procedure that reduces moisture concentration to 4–6%. Temperatures during kilning are between 40°–85° C. Typically the lower temperatures of less than 60° C. are used until the seed have a moisture content of between about 10 and 20%. Final drying is at higher temperatures of above 60° C.

The kiln-dried material (or malted seeds) may then be used directly, for example, where the recombinant protein is useful in veterinary applications (e.g., animal feed containing a an increased protein value, growth hormone or vaccine). The seed may be formulated into a mash product.

The mash may also be processed by mechanical disruption of the seeds and bringing the total protein into solution. The cellular debris may then be separated by any convenient means, such as settling, centrifugation, filtration, or the like. The supernatant or filtrate will normally include from 1 to 40 weight percent of the desired product of total protein in the medium, preferably at least about 30 weight percent.

Where the desired product is not water soluble, one may need to extract the desired product with a convenient solvent or use another process which allows for solubilization and/or extraction of the product without loss of the desired activity of the product or which allows for renaturation.

After isolation of the protein of interest from the aqueous medium, one may then purify the product in accordance with conventional ways. Since the product will be a substantial portion of the total protein present in the mixture, frequently being present in the greatest percentage of any individual protein, purification is greatly simplified. Furthermore, contaminants in the product after purification are not likely to be of physiological concern for many of the applications of the products, including therapeutic applications.

By providing for malting, seeds can be germinated under conditions where a desired product can be produced in the germinated seeds to provide for a high propc on of the total protein in the malting mash being the desired protein. By breaking the cells, separating the cellular debris from the protein, and isolating the supernatant from the mash, the protein may be easily isolated and purified, being a major component of the total protein in the medium.

As distinct from other methods of producing proteins, the subject method provides for high levels of economic production of proteins in a crude form which can be easily purified. The system lacks the potential for the production of endo and exotoxins, which is of concern with prokaryotes. The system allows for storage under ambient conditions without significant loss of seed viability or product loss. The product can be produced on demand. In this way, proteins can be produced in accordance with need, where the source of the protein can be conveniently and safely stored.

In one embodiment, the malted transgenic seeds of the present invention, containing a protein of interest, can be used as a malted seed feed product for animals. The malted transgenic seeds can be mixed with normal (i.e., non-transgenic) seeds to obtain the desired concentration of the protein of interest in an animal feed product.

The following is an example of protein production by the malting process of the present invention. Varieties of rice containing the human gene for α-1-antitrypsin (i.e., transgenic rice) are inbred to produce homozygous lines. These transgenic lines are cultivated in the field and mature seeds are harvested using conventional agricultural practices.

The transgenic seeds are transported to a malting facility (malthouse) where they are soaked (steeped) in water for 48 hours. The seeds are then transferred to malting bins where they are allowed to germinate from 2 to 4 days. During germination, the temperature and humidity of the seed bed is monitored to ensure ideal germination conditions. In some cases, chemicals such as the plant hormone, gibberellic acid, may be added to enhance the expression of the α-1-antitrypsin gene which is under the control of a gibberellic acid inducible promoter (e.g., RAmy1A, RAm3C, HV18).

After optimum germination and expression of the α-1-antitrypsin gene have been achieved, the seeds are mashed (for example, by gentle grinding) to disrupt tissues and remove the hulls from the seeds. The seed mash is suspended in a protein extraction buffer. Such a buffer typically contains protease inhibitors, reducing agents and a buffering agent (such as, "TRIS" or sodium or potassium phosphate).

The mash is agitated or stirred to ensure that all secreted protein is freed from tissues and cells. Large particulate matter, such as hull, plant tissues, and other debris are then removed by filtration or centrifugation. The supernatant is collected and chilled to reduce proteolysis of α-1-antitrypsin.

The supernatant is subjected to various purification schemes used in the wet-milling industry (e.g., hydrocloning and ion exclusion chromatography) to remove un-wanted proteins and to concentrate α-1-antitrypsin. Alternatively, ammonium sulfate precipitation can also be used to concentrate the α-1-antitrypsin.

Affinity- and ion-exchange chromatography can be used to purify the α-1-antitrypsin away from other proteins in the supernatant. The presence of α-1-antitrypsin in the various chromatographic fractions can be detected using standard photometric assays.

In another embodiment, after the transgenic seeds are transported to a malting facility (malthouse) they are dehulled and deembryonated (i.e., mechanical separation of the embryos and endosperm portions of the seed). The embryos and endosperms are separately soaked (steeped) in water for 48 hours. The seeds are treated as described above. The separated embryos are treated as follows. Expression of the RAmy3D promoters is induced in the absence of sugar and/or by the addition of chemicals, such as a plant hormone, e.g., abscisic acid.

After optimum germination and expression of the α-1-antitrypsin gene have been achieved, the embryo and endosperm portions are mixed and then mashed (i.e., gentle grinding) to disrupt seed tissues. The mash is then treated as above for purification of the α-1-antitrypsin polypeptide.

IV. Production of Recombinant Proteins Using a Cell Culture Process.

In the second aspect, the invention relates to the regulated expression of recombinant proteins in cereal cell culture. In one embodiment of the invention, the cells are derived from scutellar epithelium of cereal plants. The chimeric genes, vectors and methods described above may be implemented in the practice of this aspect of the invention. In this aspect, the invention includes modulating expression of a polypeptide in monocot plant tissue cell culture. Transgenic plant cells are produced that contain a chimeric gene having at least the following components:

(i) a transcription regulatory region inducible during seed germination, where expression mediated by said region is specifically regulatable by a small molecule. Several examples of such regions and small molecule regulators are described below; and (ii) a heterologous DNA sequence that encodes the polypeptide, where said DNA sequence is operably linked to said promoter. The chimeric gene may also contain a signal sequence to facilitate secretion from the cell of the polypeptide encoded by the heterologous DNA sequence.

The transgenic cells are cultured under conditions that facilitate plant cell growth. Expression of the polypeptide of interest is modulated by addition or removal of at least one small molecule to the plant cell culture.

For example, the principle of using different cereal α-amylase promoters to express a recombinant protein in tissue culture cells is illustrated in FIG. 1A. In this figure, the sugar-repressible promoter for the rice α-amylase gene, RAmy3D, was used to express the bacterial reporter gene, gusA, in rice. The gusA gene encodes the enzyme, beta-glucuronidase (GUS), that produces a blue chromophore in tissues expressing the gene. This chromophore can be easily detected using a histochemical staining method. As can been seen in this figure, the product of gusA is repressed in rice cells when the culture medium contains 3% sugar.

Cells or tissues derived from cereal plants can be transformed singly or together (i.e., co-transformation) with the expression constructs described above. Once integrated into the plant genome, the recombinant protein can be recovered and purified from the medium of cultured transgenic cells.

The vectors of this invention can be used to facilitate the expression and/or secretion of heterologous protein in cell culture. The plant cells are placed and maintained into suspension culture and induced through the variety of inducers described above to produce high levels of the desired heterologous protein. The protein is then isolated using conventional technology.

Because the purifications are dramatically varied for individual proteins, it is sufficient to indicate that the initial purification process will typically follow the purification process of the native protein from its host. Because the growth media of the plant suspension culture, as used in the present invention, is typically more simple than the normal host environment of the protein of interest, the purification procedures may be appropriately modified and simplified by those of skill in the art.

It is evident from the above results, that plant cells can be engineered and the cells used to propagate plants. The plant cells can be modified to provide for expression constructs that allow controlled expression of the coding sequence in the construct to provide the expression product as the major product.

By combining the technology of the present invention with well-established production methods (e.g., plant cell fermentation, crop cultivation, and product recovery), recombinant protein can be efficiently and economically produced for the biopharmaceutical, industrial processing, animal health and bioremediation industries.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The following examples are provided by way of illustration only and not by way of limitation. Those of skill will readily recognize a variety of noncritical parameters which could be changed or modified to yield essentially similar results.

EXAMPLES

General Methods

Generally, the nomenclature and laboratory procedures with respect to standard recombinant DNA technology can be found in Sambrook, et al., *Molecular Cloning—A Laboratory Manual*, Cold Spring Harbor Laboratory, Cold Spring Harbor, N.Y. 1989 and in S. B. Gelvin and R. A. Schilperoot, *Plant Molecular Biology*, 1988. Other general references are provided throughout this document. The procedures therein are known in the art and are provided for the convenience of the reader.

Example 1

Expression of β-glucuronidase Under the Control of the α-amylase Promoter in Rice Cell Culture A. Initiation of Scutellar Callus and Suspension Cultures.

Rice seeds (Oryza sativa L. cv. M202) were provided by Dr. M. Brandon (California Rice Experimental Station). Seeds were dehulled, washed three times with water, rinsed in 70% ethanol for 20 sec and then surface-sterilized in 1% sodium hypochlorite with a few drops of Tween 20 under vacuum for 20 min. Sterilized seeds were washed three times with sterile distilled water. Seven seeds were placed in 15 cm petri dishes containing LS medium with 2 mg/l 2,4-D and 30 g/l sucrose. The seeds were incubated in the dark at 28° C. and checked periodically to monitor the growth of scutellar-derived callus. Callus formation from scutellum tissue and/or embryo was visible after 5 days. After 30 to 40 days, clumps of friable calli, about 1 cm in diameter, were saved and the remaining tissue was discarded.

To initiate a suspension culture, friable calli were gently agitated in a petri dish with liquid AA medium as described by Thompson J A, Abdullah R and Cocking E C, Protoplast culture of rice (*Oryza sativa L.*) using media solidified with agarose (*Plant Sci.* 47:123–133 (1986) to reduce the calli to small clusters of cells. Cell clusters from about 20–30 clumps of calli were then transferred to a 125 ml Erlenmeyer flask and the liquid was replaced with 25 ml of fresh AA medium. The flasks were incubated in the dark on a rotary platform shaker at 110 rpm and 28° C. The primary culture was sub-cultured every 4 to 5 days with repeated screening for small cell clusters. This was accomplished by passing the culture sequentially through nylon filters of 1000 $\mu$m and 500 $\mu$m pore size. After two months of subculture, a finely divided and rapidly growing suspension culture was obtained. This culture was subsequently maintained by weekly subculture in AA medium containing 3% sucrose.

B. Construction of the RAmy3D/GUS Gene Fusion

Figure 2:
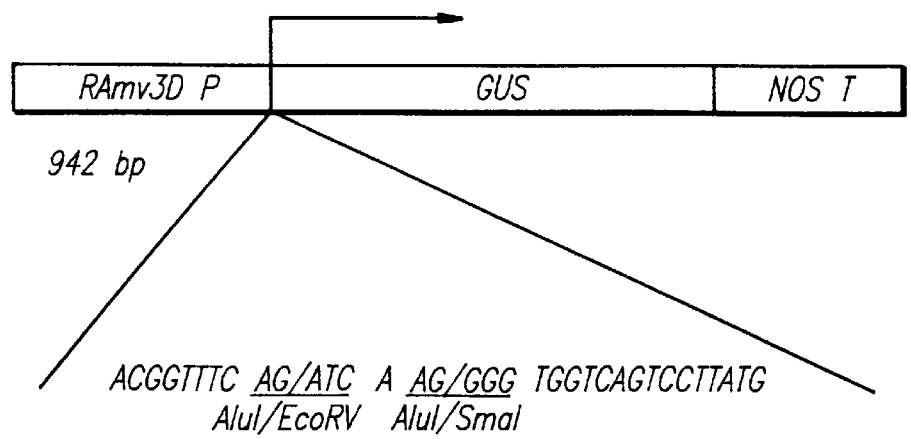
FIG. 2 is a depiction of the plasmid construction for producing transgenic seed with a RAmy3D promoter.

The RAmy3D promoter/GUS gene fusion shown in FIG. 2 was constructed in three steps. First, a 1.5 kb SalI fragment containing the promoter and part of the coding region from rice genomic clone $\lambda$OSglA as described by Huang, et al., 1990a, *Nucleic Acid Res.*, 18:7007–7014 was subcloned into pBluescript KS– to produce the plasmid plAS1.5. The AluI fragment from plAS1.5 containing 876 bp of promoter and 66 bp of 5' untranslated region was subcloned into the EcoRV site of "PBLUESCRIPT KS+" to form plAlu.

Second, a plasmid containing a promoterless GUS cassette was constructed by subcloning the HindIII/EcoRI GUS cassette from pBl101 (Jefferson R A, 1987, Assaying chimeric genes in plants: the GUS gene fusion system. *Plant Mol. Biol. Reporter*, 5:387–405) into pUC19 to form pBl201. A pUC19 polylinker in front of the GUS coding region provides convenient cloning sites for inserting promoter fragments. Third, the RAmy3D promoter fragment was inserted into the promoterless GUS plasmid to produce the plasmid p3DG. The XbaI/AluI (in HindIII site) promoter fragment from plAlu was ligated into XbaI/SmaI digested pBl201. The final 11 bp of RAmy3D 5' untranslated region was substituted by 21 bp from the polylinker resulting in the 5.83 kb plasmid, p3DG.

The junction between the RAmy3D promoter and the 5' end of the GUS gene was confirmed by DNA sequencing. DNA restriction digest, DNA gel electrophoresis, ligation, transformation, plasmid DNA isolation and DNA sequencing followed standard procedures (Sambrook, et al., *Molecular Cloning—A Laboratory Manual*, Cold Spring Harbor Laboratory, Cold Spring Harbor, N.Y. 1989.

C. Protoplast isolation and DNA transformation

Three days after subculture, a 60 ml of rice suspension culture was given a ten minute, 45° C. heat-treatment and transferred to two glass crystallizing-dishes. The AA medium was removed and the cells in each dish were mixed with the 20 ml of enzyme mixture (1% Cellulose RS, 1% Macerozyme R10 in CPW medium described by Thompson, et al., 1986, *Plant Sci.* 47:123–133. The cell walls were digested at 28° C. for 15 hours while shaking at 45 rpm.

After digestion, the protoplasts were screened through 150, 50 and 20 $\mu$m nylon filters, washed three times by centrifuging for 10 min at 80 g, and gently resuspended in 40 ml of CPW medium. Then the suspension was adjusted to 5 million protoplasts/ml.

Two and one-half million protoplasts in 0.5 ml volume were mixed with 5 $\mu$g of p3D2 DNA, 25 $\mu$g of calf thymus carrier DNA and 5 $\mu$g of pGL2 plasmid DNA carrying the CaMV 35S promoter/hph gene fusion encoding hygromycin-resistance as described by Shimamoto K, Terada R, Izawa T and Fujimoto H (Fertile transgenic rice plants regenerated from transformed protoplasts *Nature* 338:274–276 (1989)), transferred to a cuvette, placed on ice for ten min, then electroporated with a "GENE PULSER" electroporator (Bio-Rad)(300 volt/cm, 560 mF and 600 Ohms).

After being kept on ice for an additional 10 min, the protoplasts were mixed with 0.5 ml of 4× KPR medium (Thompson, et al., Supra 1986) and 1 ml of melted 2.4% "SEA PLAQUE" low gelling agarose, plated in Petri dishes and incubated at 28° C. in the dark.

Ten days after plating, the agarose in each Petri dish was separated into four pieces and transferred into a 6 cm Petri dishes containing 5 ml of liquid KPR medium. Four days later hygromycin was added to each dish to a final concentration of 50 mg/ml. Hygromycin-resistant colonies were picked and grown in liquid AA medium to form a number of cell lines. A sample from each cell line was then assayed for GUS activity by staining the cells with X-glu (Jefferson, et al., supra 1987). Cell lines having GUS activity were retained. Uniform cell lines were obtained by two additional rounds of isolating cell single cell clusters coupled with selection for GUS expression. Integration of p3DG DNA into the rice genome was verified by Southern blot analysis.

D. RNA Isolation and Dot Blot Hybridization

Total RNA was isolated from cell suspension culture using a modification of the phenol/SDS procedure Ausubel F M, Brent R, Kingston R E, Moore D D, Seidman J G, Smith J A and Struhl K: Current Protocols in Molecular Biology. (1989). Approximately one gram of cultured rice cells were ground into a fine powder with sand and 5 ml of liquid nitrogen until all the liquid nitrogen evaporated. Then 2.5 ml of TLE buffer (0.2M Tris pH. 8.2, 0.1M LiCl, 5 mM EDTA, 20 mM sodium metabisulfite) was added and grinding continued until the sample was completely liquefied.

At this point, 0.5 ml of 10% SDS, 2.5 ml of phenol and 2.5 ml of chloroform were added to the mortar sequentially and mixed well by grinding. The sample was centrifuged at 4000 g for 15 min and the aqueous phase removed and extracted with chloroform. Total RNA was precipitated by the addition of ⅓ volume of 8M LiCl and the mixture was allowed to sit overnight at 4° C. The RNA was harvested by centrifugation at 16,000 g for 30 min at 4° C. and the RNA pellet was dissolved in 0.5 ml of double distilled water treated with diethylpyrocarbonate. The RNA was extracted once more with chloroform and then precipitated with ethanol. The RNA yield was approximately 500 $\mu$g from each gram (fresh weight) of cells.

The pre-hybridization and hybridization of $\alpha$-amylase probe to the membrane under $\alpha$-amylase group-specific conditions was as previously described by Huang N, Koizumi N, Reinl S and Rodriguez R L (Structural organization and differential expression of rice $\alpha$-amylase genes *Nucleic Acids Res.* 18:7007–7014 (1990a) and Huang N, Sutliff T D, Litts J C and Rodriguez R L: Classification and characterization of rice $\alpha$-amylase multigene family. *Plant Mol. Biol.* 14:655–668 (1990b)).

Four different rice $\alpha$-amylase genes were used as probes. The RAmy1A probe, a 1.6 kb XbaI fragment from pOS103 described in O'Neill S D, Kumagai M H, Majumdar A, Huang N, Sutliff T D and Rodriguez R L (The $\alpha$-amylase genes in *Oryza sativa*: characterization of cDNA clones and mRNA expression during seed germination. *Mol. Gen. Genet.* 221:235–244 (1990)) cross hybridized with the closely related genes RAmy1B and RAmy3C under the stringency conditions used.

The RAmy3D probe, a 1.6 kb Xbal fragment from pOS137 [O'Neill, supra] was used under gene-specific conditions. The RAmy3A probe, a 3.5 kb EcoRI fragment from λOS7D (Sutliff T D, Huang N, Litts J C and Rodriguez R L: Characterization of an α-amylase multigene cluster in rice. *Plant Molecular Biology.* 16:579–591 (1991)) was used under highly stringent, gene-specific conditions. The RAmy3E probe, a 2 kb HindIII fragment including the two introns exons II and III, and the 3' end as described by Huang N, Koizumi N, Reinl S and Rodriguez R L (Structural organization and differential expression of rice α-amylase genes. *Nucleic Acids Res.* 18:7007–7014 (1990a)).

E. DNA Isolation and Southern Blot Hybridization

Total genomic DNA was isolated using a small scale CTAB procedure described by Rogers SO and Bendich A J (Extraction of DNA from milligram amounts of fresh, herbarium and mummified plant tissues. *Plant Mol. Biol.* 5:69–76 (1985)). Southern blot analysis of transformed and un-transformed cultured cells was the same as previously described in Huang N, Sutliff T D, Litts J C and Rodriguez R L (Classification and characterization of rice α-amylase multigene family. *Plant Mol. Biol.* 14:655–668 (1990b)).

The DNA probes used were the HindIII/EcoRI fragment of pBI201 (Jefferson, Supra) for the GUS gene and pOS103 as described in O'Neill S D, Kumagai M H, Majumdar A, Huang N, Sutliff T D and Rodriguez R L (The α-amylase genes in *Oryza sativa*: characterization of cDNA clones and mRNA expression during seed germination. *Mol. Gen. Genet.* 221:235–244 (1990) for rice α-amylase gene RAmy1A.)

F. Isolation of Total Protein and β-glucuronidase (GUS) Activity Assay

Total water soluble protein was isolated from suspension culture cells based on the procedure described by Jefferson, supra. A 200 mg sample of suspension culture cells was ground in a mortar and pestle for one min in the presence of sand and 0.5 ml of GUS extraction buffer (Jefferson, supra). The slurry was transferred to a 1.5 ml microfuge tube and the cell debris removed after 5 min of centrifugation at room temperature. The supernatant was saved as a crude extract of water soluble protein. The GUS activity was measured by the fluorometric assay procedure (Jefferson supra) The background level of GUS activity in control, untransformed cells was negligible.

GUS activity was also assayed in whole cultured cells by calorimetric methods (Jefferson, supra). Fresh or frozen cultured cells were put in either a 1.5 ml tube, a 3.5 cm Petri dish or a microtiter plate. Five volumes of sterile X-glu solution were added to the cells. The reaction was incubated at 37° C. for 30 min. or longer.

G. Secretion of GUS Into the Media Using the RAmy1A Promoter in Transgenic Rice Cells.

The suspension cells are removed by filtration and the filtered media is assayed for GUS activity. The assay methods are as described above.

H. Results

1. Metabolic regulation of RAmy3D and RAmy3E in untransformed rice suspension cultures.

The above experiments allow for the determination of which rice α-amylase gene(s) is metabolically regulated in rice cell cultures. Total RNA was isolated from a cell culture sampled over a period of eight days. RNA dot blots were hybridized sequentially with four different α-amylase gene probes. The mRNA levels for the RAmy1A, RAmy1B and RAmy1C genes were low and did not change significantly during the eight day period. The level of RAmy3A mRNA was also low and showed little change during the culture cycle. The levels of RAmy3D and RAmy3E mRNA were low initially, but increased significantly after five days, reaching their peak levels at 8 and 6.5 days respectively. These results are consistent with previous studies which demonstrated that RAmy3D (Group 2) and RAmy3E (Group 5) mRNA were abundantly expressed in rice cell culture while the expression of RAmy1A/RAmy1B/RAmy1C (Group 1), RAmy2A (Group 4) and RAmy3A/RAmy3B/RAmy3C (Group 3) was either low or undetectable. Other workers have found moderate expression of RAmy1A and another gene in the Ramy1 subfamily, but only in 14 day old cell cultures.

The concentration of sugar in the rice cell suspension culture medium correlates with the amount of α-amylase enzyme produced by the cells. To investigate this effect at the gene level, suspension cultures, normally maintained in medium containing 3% sucrose, were subcultured into media with 1%, 3%, 6% or 12% sucrose. RNA was isolated from cells harvested at one day and at five days after subculture. RNA dot blots were hybridized with α-amylase gene probes. All cells harvested after one day had approximately the same levels of α-amylase gene expression, presumably because none of the cultures had yet depleted the sucrose from the medium.

The mRNA levels for the RAmy3D and RAmy3E genes increased significantly after five days in the culture with 1% sucrose medium, showing induction of gene expression after the sugar was depleted from the medium. Cultures with higher initial sucrose concentrations still had only low levels of RAmy3D and RAmy3E gene expression after five days. The levels of RAmy1A, RAmy1B, RAmy1C and RAmy3A gene expression changed little in any of the cultures.

Sucrose concentrations in the culture medium were altered to test the effect on α-amylase gene repression. After four days of culture in medium with an initial sucrose concentration of 3%, cultures were subdivided and the sucrose concentration was increased to 6% and 12%. One of the cultures was washed and resuspended in sucrose-free medium (0%). Cultures were incubated for two more days and RNA was isolated for analysis by slot blot hybridization.

RAmy1A, RAmy1B, RAmy1C and RAmy3A expression levels were consistently low in all subcultures. RAmy3D gene expression was significantly reduced in subcultures supplemented with 6% or 12% sucrose, relative to that of the sucrose-free subculture. RAmy3E gene expression remained high in all treatments. Thus, within two days after the addition of sucrose to the culture media, RAmy3D was highly repressed while RAmy3E expression was relatively unchanged. It is not clear to what extent these results are due to differential transcriptional control and/or differential mRNA stability.

2. Transformation of RAmy3D Promoter/GUS Into Rice Cell Lines.

A RAmy3D promoter/GUS gene fusion was constructed and used to transform rice protoplasts. The plasmid p3DG contains 876 bp of RAmy3D 5' flanking region plus 66 bp of the 5' untranslated leader sequence linked to the GUS coding region (FIG. 2). Plasmid p3DG was introduced into rice protoplasts by co-electroporation with the plasmid pGL2 which carries the hygromycin-resistance gene. Protoplast-derived colonies were selected on hygromycin-containing medium and tested for co-transformation with the RAmy3D/GUS construct by staining a few cells from each colony for GUS activity. Two cycles of hygromycin-resistance selection and GUS activity screening were used to isolate the 3DG cell line.

DNA was isolated from the 3DG cell line and from a non-transformed control cell line, digested with BamHI and subjected to Southern blot hybridization (FIGS. 3A and 3B). When the blot was probed with the GUS gene, a strong hybridization signal to DNA from the 3DG cell line (lanes 2–5, FIG. 3A) was observed. No hybridization was seen with DNA isolated from the control cell line (panel GUS, lane 1 of FIG. 3A).

The negative result in the GUS panel (lane 1, FIG. 3A) was not due to the lack of DNA transferred to the membrane. Equivalent amounts of DNA were detected in all lanes when the same membrane was stripped of the GUS probe and rehybridized with a probe from the rice α-amylase gene RAmy1A (FIG. 3B). These bands hybridizing to the α-amylase probe have the molecular weights predicted from the DNA sequence of the RAmy1A gene.

Using the GUS probe, the 3DG cell line had the same hybridization pattern before (FIG. 3A, lane 2) and after (lane 4) the two cycles of single cell clump selection, indicating that the plasmid DNA was stably inherited as the cells proliferated.

Two types of structural evidence indicate that the RAmy3D/GUS DNA is integrated into the chromosomes of the 3DG cell line. First, Southern blot analysis revealed that the GUS gene probe hybridized exclusively to undigested genomic DNA larger than the size of the p3DG plasmid (FIG. 3A, lanes 3 & 5).

Second, digestion of the DNA from the 3DG cell line with endonuclease BamHI resulted in multiple hybridization bands (FIG. 3A, lanes 2 & 4). BamHI does not cut within the RAmy3D/GUS gene construct, so each band size represents a different sized junction fragment between the unique BamHI site in the p3DG plasmid and a BamHI site in the adjacent chromosomal DNA.

Thus, multiple copies of the RAmy3D/GUS gene construct (and at least one copy of the hygromycin-resistance gene) have been integrated into the genome of the 3DG cell line. The low molecular weight bands and the faint bands of hybridization on the Southern blot probably represent fragments of the RAmy3D/GUS gene construct inserted into the rice genome.

3. Metabolic Regulation of RAmy3D/GUS in Transgenic Rice Cell Lines.

Gene expression and enzyme activity for GUS was assayed in the 3DG cell line to determine whether the promoter fragment in the RAmy3D/GUS construct contains all of the cis-elements necessary for proper- expression and metabolic regulation of the gene. Dot-blot hybridization using a GUS gene probe indicated that the mRNA level from the GUS gene in 3DG cells increased as sugar was depleted from the culture medium.

Figure 4:
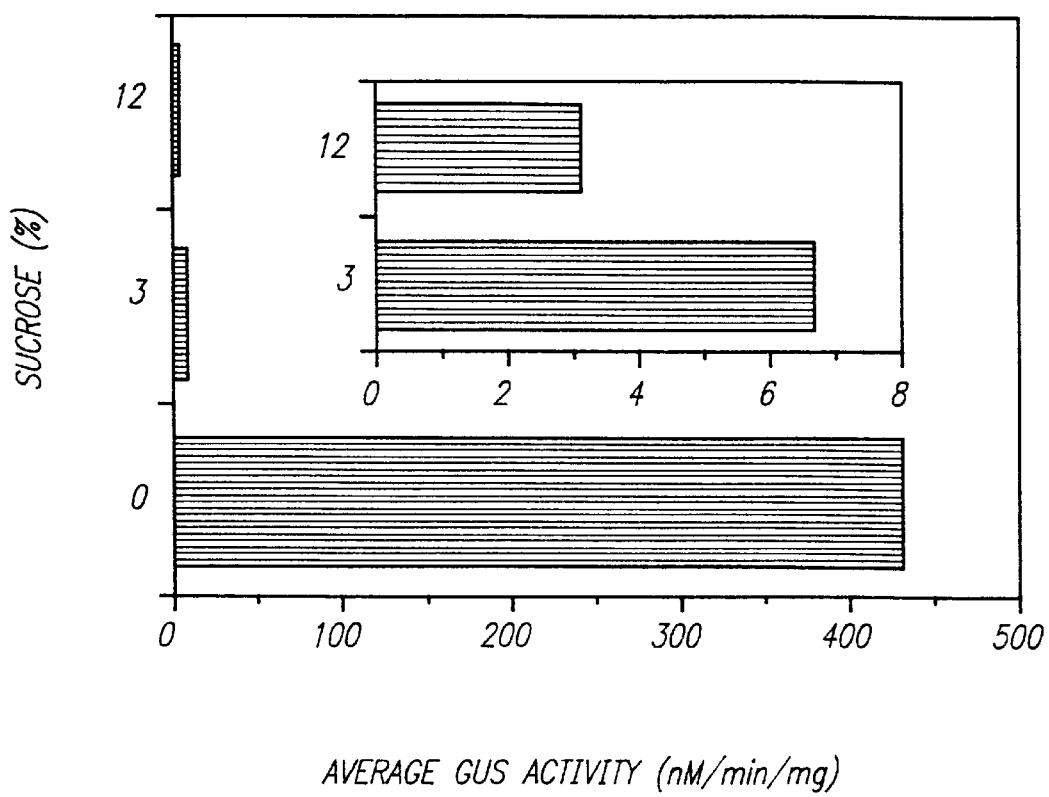
FIG. 4 provides the results of a fluorescent assay detecting GUS.

The GUS enzyme assay was used to test for the expression of RAmy3D/GUS in response to various concentrations of sucrose in the culture medium. The 3DG cell line was subcultured into modified AA medium containing 0%, 3% or 12% sucrose. Three days later, water soluble protein was extracted and assayed for GUS by the fluorescence assay (FIG. 4). The GUS activity in cells cultured with no sucrose was 65-fold higher than that of cells grown in 3% sucrose and 130-fold higher than that of cells grown in 12% sucrose. Thus, the transcriptional activity of the RAmy3D promoter was greatly repressed in the presence of high levels of sucrose while being highly induced under conditions of sugar deprivation.

Figures 5, 6D:
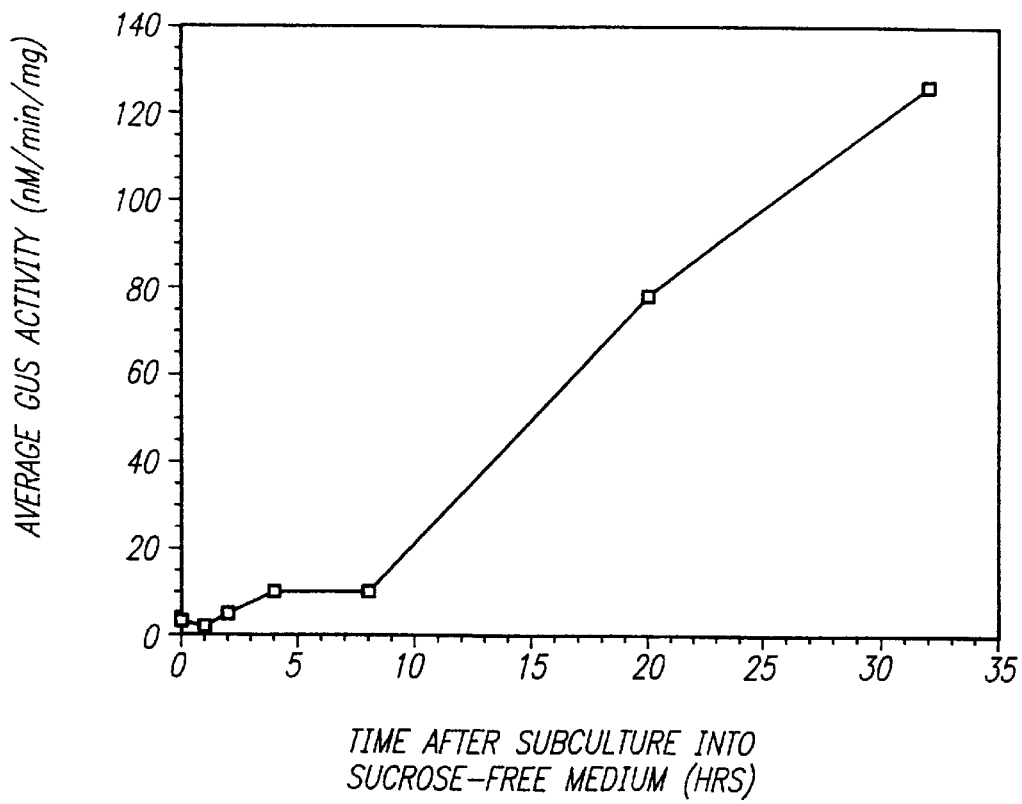
FIG. 5 provides the results of a fluorescent assay detecting GUS from cells free of sucrose.
FIG. 6D is a table comparing sequence homology between α-amylase promoters.

The timing of RAmy3D promoter induction in response to sugar deprivation was studied by incubating 3DG cells in sucrose-free medium. There was little or no increase in GUS activity during the first eight hours of incubation (FIG. 5). GUS activity increased rapidly between eight to thirty-two hours after sub culturing. The expression and metabolic regulation of the RAmy3D/GUS gene construct resembles that of the endogenous RAmy3D gene.

These results are similar to those of others who observed an increase in total α-amylase mRNA beginning 4 hours after the start of sugar deprivation. Thus, the cis-element(s) responsible for metabolic regulation must be contained in the 942 bp promoter region on the RAmy3D/GUS construct.

The expression of the GUS gene product was visualized using histochemical staining methods (Jefferson, supra) as seen in FIG. 1A where cell cultures incubated in the absence of sugar show blue staining with relatively high blue staining evident and where 3% sugar repressing the expression of the GUS gene product with relatively less blue staining is evident.

4. Promoter Sequence Analysis

Promoter sequences for RAmy3D and RAmy3E were compared to gain additional insight into the metabolic regulation of these genes. Two regions of sequence similarity were previously identified in the promoters of these genes. One of these regions consists of a 31 bp GC-rich sequence that is 71% identical between the RAmy3D and RAmy3E genes. This sequence is not found in the RAmy1A promoter (FIG. 6A–6C which compare the percent of G+C in the promoter regions of the 1A, 3D and 3E promoters, respectively) or in any other rice α-amylase promoter. This sequence is found at position-264 in RAmy3D (FIG. 6D) and contains three nearly perfect repeats of a hexanucleotide sequence composed solely of G and C residues.

The RAmy3E promoter contains one complete and one partial copy of the hexanucleotide repeat sequence. The tandem duplication of GC-rich hexanucleotides in the 31 bp GC-rich sequences is reminiscent of binding sites for the mammalian transcription factor Spl.

An 11 bp sequence containing part of the GC-rich hexanucleotide is also found in the RAmy3D and RAmy3E promoters (FIG. 6D). These sequences may represent cis-acting elements involved in the metabolic regulation of the rice α-amylase genes. GC-rich promoter sequences have also been identified in the metabolically regulated α-amylase genes of Aspergillus oryzae.

Example 2

Secretion of Heterologous Protein Across the Aleurone Layer of an Intact Rice Seed Using the RAmy1A Promoter A. Plasmids Plasmids were constructed using standard recombinant DNA methods (Ausubel, et al., 1989, *Current Protocols in Molecular Biology*, NY John Wiley and Sons and Sambrook, et al., supra, 1989). The RAmy1A gene of rice was chosen because of its responsiveness to GA (O'Neil, et al., 1990 *Mol. Gen Genet.*, 221, 235–224) and because it is the most active of the α-amylase genes expressed during seed germination (Karrer, et al., 1991, *Plant Mol. Biol.*, 16, 797–805).

Two regions of the RAmy1A promoter were fused to the gus A reporter gene to produce plasmids pH4/GUS (−748 to +31) and pE4/GUS (−232 to +31). Both promoter regions contain three conserved sequences ($^{-214}$CCTTTT$^{-209}$, $^{-147}$TAACAAA$^{-141}$, and $^{-130}$TATCCAT$^{-124}$) found in all the GA-responsive cereal α-amylase genes examined to date (Huang, et al., 1990). An additional pyrimidine box is present in pH4/GUS at position-312.

The promoter for the RAmy1A gene was subcloned as a 2.3 kb DNA fragment from the rice genomic DNA clone (lOSg2) into "pBLUESCRIPT M13+KS." The nucleotide sequence of this promoter has been described in Huang, et al., 1990 *Nuc. Acids Res.* 18:7007–7014. The principal features of these constructs consists of the b-glucuronidase gene (gusA), together with the transcriptional terminator of the nopaline synthase gene from pBI101 as reported in Jefferson, 1987 *EMBO Journal* 6:3901–3907.

The expression cassette was inserted into the SmaI site of "pBLUESCRIPT" and designated pBSGUS. RAmy1A (promoter)/gusA gene fusions were constructed by inserting restriction fragments containing the RAmy1A promoter into pBSGUS. The restriction fragments used to make constructs were the PstI-HindIII fragment (−748 to +31, pH4/GUS) and the Psfl-EcoRI fragment (−232 to +31, pE4/GUS). The coordinates used to describe these restriction fragments are based on transcription start point for RAmy1A (Huang, et al., supra 1990).

B. Rice Transformation

RAmy1A/GUS plasmids were co-transformed into rice protoplasts (Oryza sativa L. japonica varieties, Nipponbare, Kinuhikari and Toride-1) by electroporation as previously described (Shimamoto, et al., 1989, Fertile transgenic rice plants regenerated from transformed protoplasts, *Nature*, 338:274–276 and Kyozuka and Shimamoto, 1991 Transformation and regeneration of rice protoplasts, in *Plant tissue Culture Manual* (Lindsey, K. ed). Dordrecht:Kluwer Academic Publishers B1:1-16).

The hph gene (hygromycin phosphotransferase) was used as the selectable marker in these studies. Hygromycin B resistant calli were screened for GUS activity by incubating a portions of calli with X-glucuronide solution (Jefferson, 1987 supra). GUS positive calli were further cultured and plants were regenerated from these callus cultures.

C. Southern Blot Analysis

The GUS positive R1 plants, derived from two lines each of H4/GUS and E4/GUS primary transgenic lines, were used for Southern blot analysis. Total genomic DNA was isolated from mature leaves, digested by the restriction enzyme EcoRI and transferred onto a positively charged nylon membrane (Amersham). The coding region of the gusA gene was labeled and amplified with digoxigenin11-dUTP by polymerase chain reaction and used for probing the intact RAmy1A/gusA genes. Hybridization and chemiluminescence signal detection were performed according to manufacturer's specifications (Boeringer Mannheim Biochemica).

D. GUS Assays

For histochemical analysis of GUS activity, germinating seeds were hand-cut with a razor and stained with X-glucuronide solution (5-bromo-4-chloro-3-indolyl glucuronide) as previously described in Kyozuka, et al., 1991 supra and Terada, et al., 1993, *Plant J.* 3:2412–252. For quantitative analysis, crude extracts from transgenic rice seeds were used for fluorometric assays of GUS activity as described previously (Kyozuka, et al., 1991; Terada, et al., 1993).

For developmental studies, transgenic R1 seeds were pealed off, sterilized with 10% NaOCl for 10 min and washed with distilled water. Seeds were germinated in plastic wells containing water for 2, 4, 6, and 8 days at 30° C. under light.

For quantitative measurements of GUS activity germinating seeds were divided into the embryo and endosperm portions. In the case of the embryo, residual amount of endosperm, roots and shoots were removed before the assay.

For the analysis of hormonal regulation of the RAmy1A/gusA chimeric genes, transgenic R1 seeds were deembryonated and the embryoless seeds and sliced longitudinally into three pieces. Each slice was treated with acetate buffer (10 mM sodium acetate pH 5.2), $10^{-7}$M GA3 in acetate buffer, $10^{-7}$M $GA_3$ and $10^{-5}$M ABA in acetate buffer, for 4 days at 30C in the dark. Treatment slices were then used for the histochemical and the quantitative GUS assays.

E. Results

1. Southern Blot Analysis of Transgenic Rice Plants

Figure 7A:
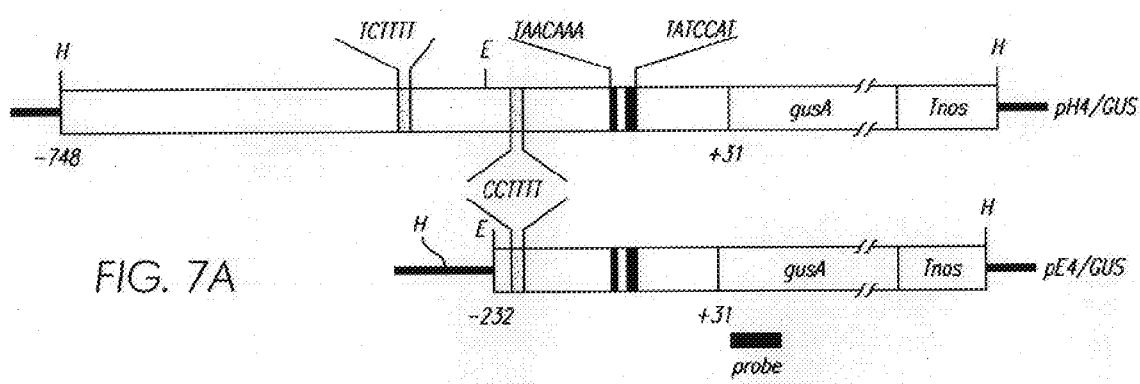
FIG. 7A depicts the construct of two gene fusions used to express GUS in rice seed.
Figure 7B:
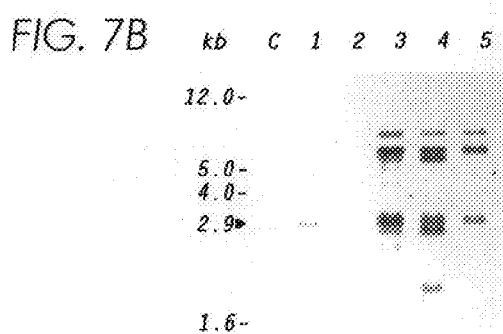
FIGS. 7B and 7C show the results of Southern blots demonstrating stable transmission of the GUS gene to rice progeny.
Figure 7C:
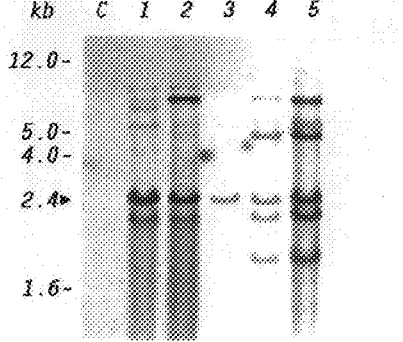

Southern blot analysis confirmed the presence of H4/GUS and E4/GUS gene fusions in the rice genome using the coding region of gusA as a probe (FIG. 7A). The results indicated that complete sequences of the H4/GUS and E4/GUS chimeric genes were present in transgenic plants and that the gusA gene was stably transmitted to the progeny (FIGS. 7B and 7C). In addition to the complete copies of the transgenes, several rearranged copies were also detected. The copy number of intact chimeric genes was estimated to be 1–3 per haploid genome.

2. GUS Activity in Transgenic Rice Seeds

Figure 8B:
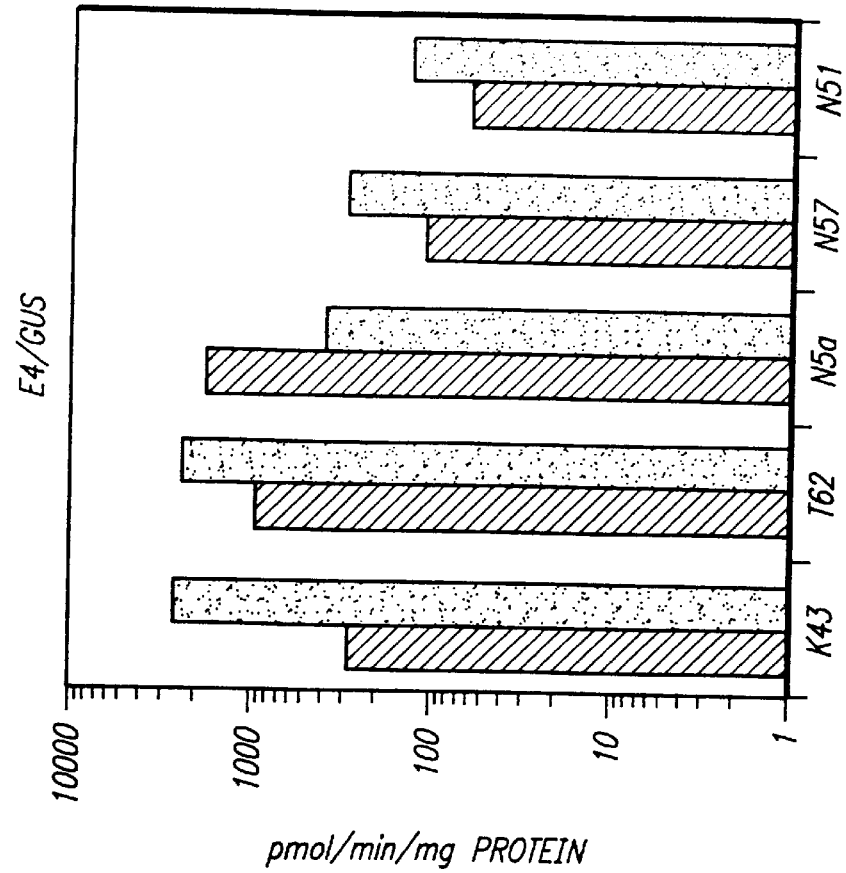
FIGS. 8A and 8B are fluorometric measures of the expression of GUS using the H4 (FIG. 8A) and E4 (FIG. 8B) constructs in different transgenic rice seed.
Figure 8A:
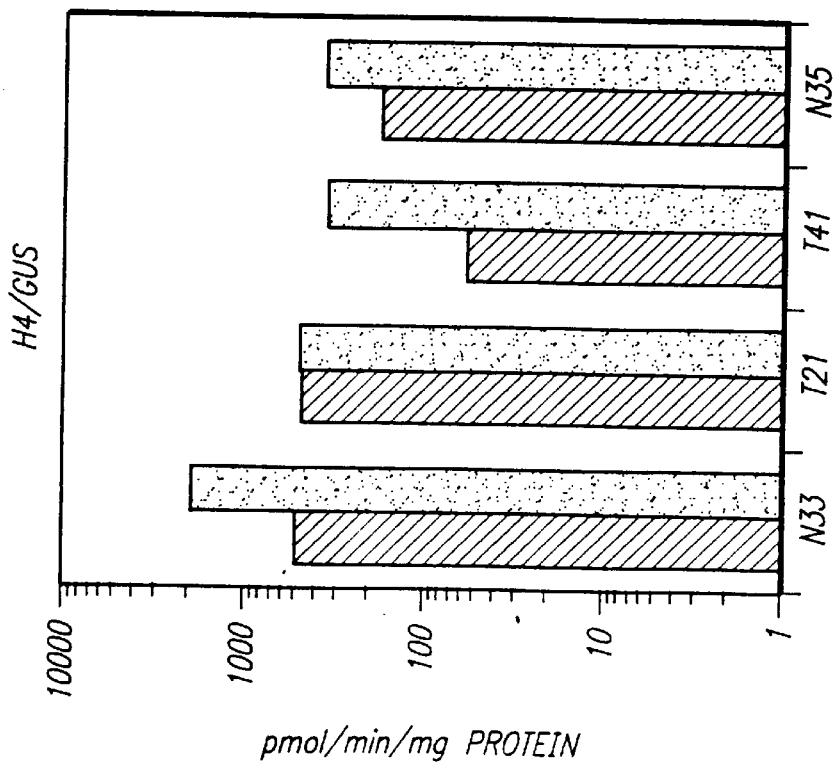
Figure 10D:
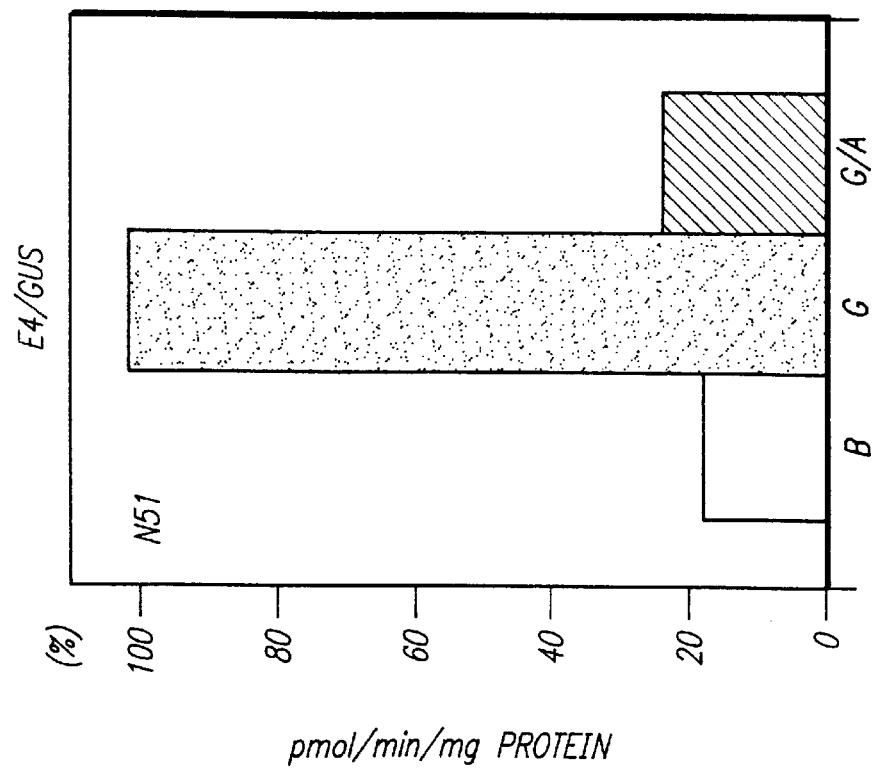
Figure 10C:
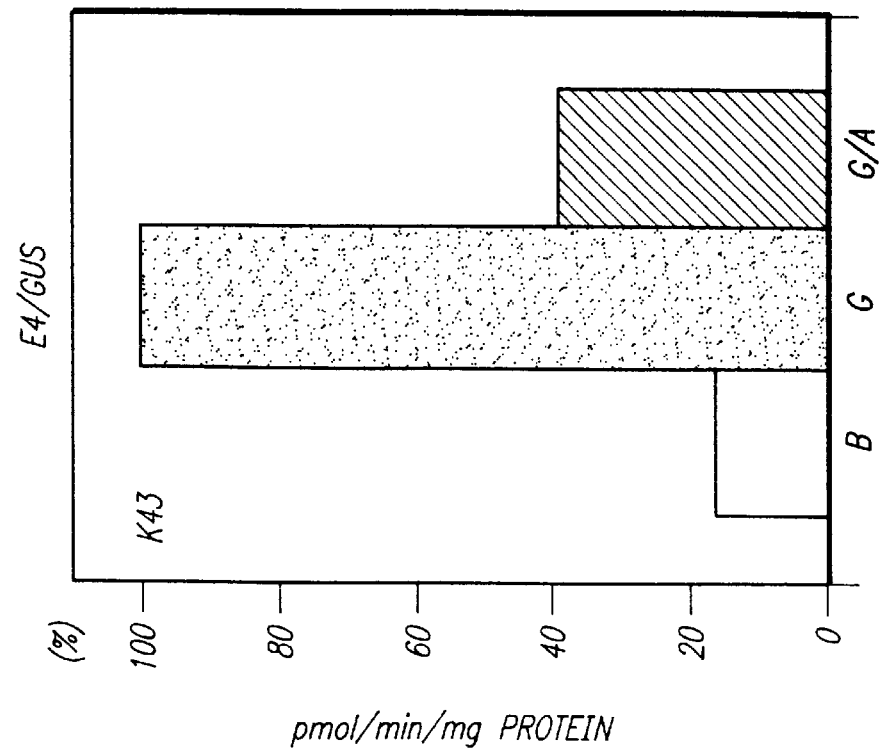

To compare the relative expression levels of the H4/GUS and E4/GUS genes, the embryos and endosperms of germinated transgenic seeds were separated and the GUS activity in each tissue was measured fluorometrically (FIGS. 8A and 8B). GUS assays of endosperm tissue were performed at 6 days of germination, the time when α-amylase expression in the aleurone layer is at its highest (FIGS. 9A–9D).

Histochemical examination of 6-day germinated seeds showed that GUS activity was restricted to the scutellum of the embryo and the aleurone layer of the endosperm. In all four lines transformed with the H4/GUS gene, the aleurone activity (partially shaded bars) was higher than the scutellum activity (cross-hatched bars) (FIG. 8A). Similarly, four of the five lines transformed with E4/GUS gene showed GUS activity to be higher in the aleurone than in the scutellum (FIG. 8B). Comparisons between H4/GUS and E4/GUS transformed lines, revealed no significant differences in GUS activity in the scutellar and aleurone tissues.

3. Temporal and Spatial Regulation of RAmy1A/GUS Expression During Germination of Transgenic Rice Seeds To investigate the role of the RAmy1A promoter in the temporal and spatial expression of heterologous genes during rice seed germination, histochemical and quantitative GUS assays on transgenic seeds were performed. Histochemical analysis of the H4/GUS chimeric gene showed that GUS activity could be detected in the scutellar epithelium after 2 days of germination and that this activity spread into the adjacent aleurone layer by day 4. On day 6, the GUS expression in the aleurone layer increased to the extent that it covered all portions of the seed.

To quantify the levels of GUS activity revealed by histochemical analysis, the GUS activities of germinating seeds derived from two H4/GUS transgenic lines (T21 and N33) were measured (FIGS. 9A and 9B, respectively). Scutellar GUS activity (open circles) appeared on da 2, peaked on day 4 and decreased thereafter.

In contrast, aleurone GUS activity (closed circles) was first detected on day 4, peaked on day 6 and decreased sharply by day 8. These results clearly show that the RAmy1A1GUS fusion genes are differentially regulated in scutellum and aleurone tissues during rice seed germination.

Similar experiments were performed on seeds from two lines of rice (K43 and T62) transformed with the E4/GUS gene fusion (FIGS. 9C and 9D, respectively). Histochemical assays revealed patterns of expression nearly identical to those observed for the H4/GUS gene. Quantitative assays of GUS activity in the scutellar and the aleurone layers of germinated seeds indicated that the E4/GUS gene is expressed in the scutellum on day 2 and peaks at day 4. GUS activity in the aleurone layer is first detected at day 4 and peaks on day 6 (FIGS. 9C and 9D). These results show that the −748 to +31 region in the H4/GUS gene and the −232 to +31 region in the E4/GUS gene, function identically with respect to the localization of expression and the developmental regulation during seed germination.

4. Hormonal regulation of the RAmy1A/GUS genes in the aleurone layer of transgenic rice seeds To examine effects of exogenously GA and ABA on the expression of the H4/GUS and E4/GUS genes in seeds, deembryonated seeds were cut into three slices and each slice was treated with GA or a combination of GA and ABA. The histochemical examination of the H4/GUS seed slices treated with GA-free buffer showed no GUS activity. However, seed slices treated with GA showed GUS activity in the aleurone layer. The observed induction of the GUS expression by GA was suppressed by addition of ABA. Similar GA induction of GUS in the aleurone layers of pE4/GUS transformed seeds was also observed.

In an attempt to quantify GA induction of the RAmy1A promoter in transgenic seeds, GUS activity was measured for both GA, and GA+ABA treated seeds (FIGS. 10A–10D). A 10 to 40-fold increase in GUS activity was observed after GA treatment of H4/GUS (FIGS. 10A and 10B) and E4/GUS (FIGS. 10C and 10D) seeds. When ABA was added along with GA, the GUS activity was suppressed to a level just above background. The degree of GA induction and ABA suppression was similar for both H4/GUS and E4/GUS derived seeds.

While the invention has been described with reference to specific methods and embodiments, it will be appreciated that various modifications and changes may be made without departing from the invention.

It is claimed:

1. A transgenic monocot plant seed having an endosperm surrounded by an aleurone or scutellar epithelium layer, said seed being stably transformed with a chimeric gene having (i) a transcriptional regulatory region inducible during seed germination, by adding or removing a small molecule, (ii) a heterologous first DNA sequence encoding a protein, and (iii) a second DNA sequence encoding a signal polypeptide, where said second DNA sequence is operably linked to said transcriptional regulatory region and said first DNA sequence, and where said signal polypeptide is in translation-frame with said protein and is effective to facilitate secretion of said protein across said aleurone or scutellar epithelium layer into the endosperm, wherein adding or removing said small molecule to said seeds, during seed malting, is effective to upregulate said transcriptional regulatory region, thereby to induce expression of said protein and secretion of said protein from the aleurone or scutellar cells into the seed endosperm.

2. The seed of claim 1, wherein the seed is from a cereal plant selected from the group consisting of wheat, rice, oats, rye, corn, sorghum, millet and barley.

3. The seed of claim 2, wherein the cereal seed is barley.

4. The seed of claim 2, wherein the cereal seed is rice.

5. The seed of claim 1, wherein the regulatory region is from an α-amylase gene selected from the group consisting of RAmy1A (SEQ ID NO:2), RAmy3B, RAmy3C, RAmy3D, HV18 (SEQ ID NO:1) and RAmy3E, and RAmy2A.

6. The seed of claim 5, where said promoter is from the RAmy3D gene or a homolog thereof.

7. The seed of claim 5, where said promoter is from the α-amylase RAmy1A or HV18 gene or a homolog thereof.

8. The seed of claim 1, wherein the protein is a growth factor.

9. The seed of claim 1, wherein the protein is a vaccine.

10. A plant seed composition produced by (i) malting the seeds of claim 1 under conditions in which said small molecule is added or removed to induce heterologous protein expression, and (ii) forming a mash containing endosperm tissue from the seed.

11. The composition of claim 10, wherein the heterologous protein is a growth hormone.

12. The composition of claim 10, wherein the heterologous protein is a vaccine.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
( A ) LENGTH: 820 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: 1..820
( D ) OTHER INFORMATION: /standard_name= "HV-18"

( x i ) SEQUENCE DESCRIPTION: SEQ ID NO:1:

```
GGATCCTAGC  TACGGACAGC  GCCCCGGTTA  TGGAGGCCGA  CAGCCGCGGC  GCGCGGCTGC    60
GTAGCAGTGC  AGCGTGAAGT  CATAGATAGA  CTGTAGAGGG  CATGGCGGCA  AGTGAAAACA   120
CACTTCCGTT  TGTTCTGTTG  AGTCAGTTGG  ATCTGCTTTG  GCCTGGCGAT  AACGTCTCCG   180
GCCATTGTTT  ATCACGGCGC  CTGCTTATCC  CTCCGAAAGT  TTGAGCAAAA  GGTGCAGCTT   240
CTTTCTAGTA  CAGAAATGAC  GTCCAGAGTT  GCAGCAACCC  ATTCGGAACT  CCTGGTGGAT   300
GCCAACGAAA  TTAAATGGGA  TAAAACTTAG  TGAAGAATCT  ATATTTCTT   GCAACAACAT   360
ACTCCTACCC  TCACGAATTG  AATGCTCATC  GAACGAATGA  ATATTTGGAT  ATATGTTGAT   420
CTCTTCGGAC  TGAAAAAGTT  TGAACTCGCT  AGCCACAGCA  CACTATTCCA  TGAAAAATGC   480
TCGAATGTTC  TGTCCTAGAA  AAACAGAGGT  TGAGGATAAC  TGACGGTCGT  ATTGACCGGT   540
GCCTTCTTAT  GGAAGGCGAA  GGCTGCCTCC  ATCTACATCA  CTTGGGCATT  GAATCGCCTT   600
TTGAGCTCAC  CGTACCGGCC  GATAACAAAC  TCCGGCCGAC  ATATCCACTG  GCCCAAGGA    660
GCATTCAAGC  CGAGCACACG  AGAAAGTGAT  TTGCAAGTTG  CACACCGGCA  GCAATTCCGG   720
CATGCTGCAG  CACACTATAA  ATACTGGCCA  GACACACAAG  CTGAATGCAT  CAGTTCTCCA   780
TCGTACTCTT  CGAGAGCACA  GCAAGAGAGA  GCTGAAGAAC                           820
```

( 2 ) INFORMATION FOR SEQ ID NO:2:

( i ) SEQUENCE CHARACTERISTICS:
( A ) LENGTH: 2389 base pairs ( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: 1..2389
( D ) OTHER INFORMATION: /standard_name= "RAMY-1A"

( x i ) SEQUENCE DESCRIPTION: SEQ ID NO:2:

| | | | | | | |
|---|---|---|---|---|---|---|
| CTGCAGGCAT | GCGAGAGGCA | CGGGGTTCGA | TTCCCCGCGT | CTCCATCGGC | ACTGTTTTTT | 60 |
| AACATCAAAC | GCTGTTCGAT | CCACTATCTG | TTAATTTCGC | AAACACAACT | AAATCTTTTT | 120 |
| TTTTTTTTGC | CGGTGCGTGC | AGTGTGACGT | CCAAGGCATG | GCGCATTGGC | GCCTCCCCTC | 180 |
| TTTCCCTTGA | TCTTTTCATC | AGTTCGTTCT | TCTTGCAGAA | AAGCTGTTCT | GTTAAGTCGG | 240 |
| TTCCGATCTG | CTCTTGGGCT | CTTGCCAGAA | ACAACCTGTG | TACGCCAGAC | TTATCAAGCC | 300 |
| AACCATCCTG | ATGAGCCTCT | GCTTATACAA | GCCTTTGACT | CCAAAAAGGA | CGAGGAGGCT | 360 |
| TGCAGCCGCA | CGGAAATAAG | CCGACCGATC | CTTTATTGCT | CTATCTTTTT | CCCTTGGAAT | 420 |
| AAAAAACAGC | CCAATTAAAA | TCTGGGATGA | AACTATGGCT | AGCTGTTCGC | GGTGTCAGTT | 480 |
| CTCGGGACGC | TACCGTTGTT | TTGTTTGAAC | CGGAATGTTC | AGGGCGGTTC | ACACCATAGA | 540 |
| CTTGGAGCCA | AGTGGTTCCA | TCCACAAAAT | TTTCTCATCT | TGAATATTCT | GTTATCTGCC | 600 |
| TCGACAGACG | CACCATATCC | TGTGTTCAGG | AATGAATGTG | CTACAGCCAA | CGTGCTGCAT | 660 |
| GAAATTTGCT | GAAATCGTGC | TAAAATGTGC | ATGGCAACAG | GAACCTGATG | CCCTGGTCCT | 720 |
| GTGGAACTGC | CACGGGAAAG | TATTTTTTAT | AGCTAGGTGC | AATCGTATCT | AGGTGTATAC | 780 |
| ATGTCACCTA | CATAGCTACT | CCCCTTTATC | TTAAAATATA | ATAATTTTTA | ACTCTCAGTA | 840 |
| TTTGTCCTAA | AATATAACAA | ATTCTCCATC | AACATTATCT | TCCCAACCAA | TCACAACCCT | 900 |
| TCATCATTAA | TTTTTTCCCC | CTACCTCCAC | TACTCATCTA | ATCACAACCC | TCCAACACTC | 960 |
| ACTTCTATCT | ACTTTCTTAA | TAACTGTCTT | CAACCCTAAA | ACTTCTTATA | TTTTAGGACG | 1020 |
| GAGGGAGTAT | CTAAATATTT | CATAAAAAAA | ATGTTAAGAT | AGATAAAGAA | GATATAAACC | 1080 |
| CACTATGCAA | ACATGCACAT | CAAAATTTAA | TTTACAGTAA | AGAAACAGAA | ATAACATATT | 1140 |
| CTATTTGTGC | TGGAGATGTA | CTGTTCACAA | TATTGTTTTT | TTATTTTTA | TTTATCTGAT | 1200 |
| TATATATCTG | TTTCAGCCTT | GCATGGTTGT | GTATGTTTGT | GTATAGACTT | ATGCCATTGT | 1260 |
| GATTGATGCT | ACCAATTATT | TTCAGACTAT | TTTTTATAG | AGGAATTTTA | TAGTTCTTGA | 1320 |
| GAAAATACCT | TGAAGTATCT | AAATTTTACA | CTAAAATTGT | TGGTACCTTG | AGGTACAAAG | 1380 |
| TACCTAGAGG | TACCAAATTT | TACTAGAAAA | TTGTGGCACC | TTTAGGTACC | TTCTCAAAAA | 1440 |
| TAGTACAATT | ATGGGCCGTT | TTGGATTTAG | TGCCAAAACG | TGCTCTACAA | ATATTTGAT | 1500 |
| AGTTTGAACA | GTGCATAAGA | CGGGTTTGGT | TTGAAGCCAA | ATCATTGGCA | TTGCCAATGT | 1560 |
| CCAATTTGAT | ATTTTCTATA | TTATGCTAAA | AGCTTGGTTC | TAAATTGGCC | TCCAACCAAA | 1620 |
| TACAACTCTA | CTCTACCAAA | AAATTTGTAG | TGCCAAAACT | TGCCTAGGTT | TTGTCACTAC | 1680 |
| CAACATTTTG | GTAAGTATTA | AACCAAACAA | GCCCTACATT | TTTTTATGTA | CATTTAAGTT | 1740 |
| GTATGTAAAT | GATGGGTGCG | GTTGCACCTA | GGTGAAAAAA | AATACATATT | CGCCACAACT | 1800 |
| CGCAACATGT | ACCAATTCAG | CAGCAAGTGT | AAGAGAGAAG | ATTTCTCTCG | TTTTACACGC | 1860 |
| GCACGTTCAA | TTCCTGAACT | ACTAAACGGT | ATGATTTTTT | GCAAAAATTT | TCTATAGGAA | 1920 |
| AGTTACTTAA | AAATTATATT | AATCTATTTT | TAAAATTTAA | AATAGTTAAT | ACTCAATTAA | 1980 |
| TTATACGTTA | ATGGCTCAGC | TCGTTTTGCG | TACATTCTCA | ATCGATTCTT | TTCCTCTGCT | 2040 |

| CTCAAATGCT | CTGTGTGCGA | TCAGGTATTC | ATGTTCAGCT | CGCACAAGCA | CAAGCAAGAC | 2100 |
| AGATGGAATT | CCTACTGACC | TGCGCCTTTT | GAGTCGCTCC | AACTCTCAAA | GTCTCAAGGC | 2160 |
| CATTAAATTG | CCTATGGGCT | CACCAGCCAA | TAACAAACTC | CGGCTGTTAT | CCATCCAATC | 2220 |
| CAGTGTCCCA | AAGCAACATT | CAAGCCCAGC | CAGGCCTCCA | AAAGTTGCAA | GTTGAGCATG | 2280 |
| GCAAAATCCC | CGGCAATTCT | CGACTATAAA | TACCTGACCA | GACACACCCA | GGAGCTTCAT | 2340 |
| CAATCATCCA | TCTCCGAAGT | GTGTCTGCAG | CATGCAGGTG | CTGAACACC  |            | 2389 |

(2) INFORMATION FOR SEQ ID NO:3:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..31
        (D) OTHER INFORMATION: /standard_name= "31 bp RAmy3D"

(xi) SEQUENCE DESCRIPTION: SEQ ID NO:3:

| GAGACCGGGC | CCCGACGCGG | CCGACGCGGC | G | 31 |

(2) INFORMATION FOR SEQ ID NO:4:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..31
        (D) OTHER INFORMATION: /standard_name= "31 bp RAmy3E"

(xi) SEQUENCE DESCRIPTION: SEQ ID NO:4:

| GAGAGCTCGC | GCCGCCTCGA | TCGGCGCGGC | G | 31 |

(2) INFORMATION FOR SEQ ID NO:5:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..11
        (D) OTHER INFORMATION: /standard_name= "11 bp RAmy3D"

(xi) SEQUENCE DESCRIPTION: SEQ ID NO:5:

| TTCCGGCTTG | C | 11 |

(2) INFORMATION FOR SEQ ID NO:6:

(i) SEQUENCE CHARACTERISTICS:
        (A) LENGTH: 11 base pairs
        (B) TYPE: nucleic acid
        (C) STRANDEDNESS: single (D) TOPOLOGY: linear (ii) MOLECULE TYPE: DNA (genomic)

(ix) FEATURE:
  (A) NAME/KEY: misc_feature
  (B) LOCATION: 1..11
  (D) OTHER INFORMATION: /standard_name= "11 bp RAmy3E"

(xi) SEQUENCE DESCRIPTION: SEQ ID NO:6:

TTGCGGCTTG C                                                          11

(2) INFORMATION FOR SEQ ID NO:7:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: misc_feature
    (B) LOCATION: 1..12
    (D) OTHER INFORMATION: /standard_name= "Taka-amylase"

(xi) SEQUENCE DESCRIPTION: SEQ ID NO:7:

CGGCCCGTCG GC                                                         12